United States Patent
Smith

(10) Patent No.: US 10,902,213 B2
(45) Date of Patent: Jan. 26, 2021

(54) SYSTEMS AND METHODS FOR CONVERTING HUMAN INTERACTIONS TO POPULATE AN ELECTRONIC FORM

(71) Applicant: JoshCo Tech, LLC, Las Vegas, NV (US)

(72) Inventor: Joshua Smith, Chula Vista, CA (US)

(73) Assignee: JOSHCO TECH, LLC, Las Vegas, CA (US)

( * ) Notice: Subject to any disclaimer, the term of this patent is extended or adjusted under 35 U.S.C. 154(b) by 0 days.

(21) Appl. No.: 16/576,718

(22) Filed: Sep. 19, 2019

(65) Prior Publication Data

US 2020/0097548 A1    Mar. 26, 2020

Related U.S. Application Data

(60) Provisional application No. 62/736,381, filed on Sep. 25, 2018.

(51) Int. Cl.
| | |
|---|---|
| *G06F 17/20* | (2006.01) |
| *G06F 40/30* | (2020.01) |
| *G06F 16/908* | (2019.01) |
| *G06F 16/93* | (2019.01) |
| *G06F 40/174* | (2020.01) |
| *G16H 10/20* | (2018.01) |

(52) U.S. Cl.
CPC ............ *G06F 40/30* (2020.01); *G06F 16/908* (2019.01); *G06F 16/93* (2019.01); *G06F 40/174* (2020.01); *G16H 10/20* (2018.01)

(58) Field of Classification Search
CPC ...... G06F 40/174; G06F 40/30; G06F 16/908; G06F 16/93; G16H 10/20
See application file for complete search history.

(56) References Cited

U.S. PATENT DOCUMENTS 8,171,390 B1   5/2012  Channakeshava
2019/0073348 A1*  3/2019  Cheesman ............ G06F 40/174

FOREIGN PATENT DOCUMENTS

CA          2750930 A1   2/2012
WO       2015091496 A1   6/2015

* cited by examiner

*Primary Examiner* — Keith D Bloomquist
(74) *Attorney, Agent, or Firm* — Patterson + Sheridan LLP

(57) ABSTRACT

Systems and methods are disclosed herein for processing human interactions and for populating an electronic form. For example, a system is disclosed having a database, a user interface, and a platform server. The database may store original forms, abbreviated forms corresponding to the original forms, and sets of conversion rules corresponding to the original form. The user interface is configured to receive data related to at least one abbreviated form, wherein the data is based on client inputs into fields of the at least one abbreviated form. The platform server extracts input data from the at least one abbreviated form, populates the original form using the input data and conversion rules corresponding to the original form to generate a completed original form, and transmits the completed original form to a client via the at least one user interface.

18 Claims, 23 Drawing Sheets

Mini DBQ (Disability Benefits Questionnaire)

Mental Disabilities

Please answer the following questions as completely and accurately as possible. This information is used to provide the VA with situations in which your PTSD or mental condition symptoms are seen. Only include information about situations that occurred during or after your active duty military service. It is important that information prior to your active duty service be excluded:

RELEVANT SOCIAL, MARITAL, FAMILY HISTORY (For example: Divorced, four children, two from ex-wife. Strained relationship with kids/ex-wife, not too involved in their lives, provide only financial support. Tend to isolate myself and don't go out with friends/family)

RELEVANT OCCUPATIONAL AND EDUCATIONAL HISTORY (For example: Increased absenteeism due to mental symptoms. Decrease in work quality/productivity. Tension with coworkers/supervisor.)

RELEVANT MENTAL HEALTH HISTORY (For example: Currently attending counseling and therapy with VA once every 6 months with little improvement. Prescribed Lorazepam and Citalopram)

RELEVANT LEGAL AND BEHAVIORAL HISTORY (For example: None reported -OR- DUI in 2013)

VBA-MDBQ-2019-01

FIG. 4A

RELEVANT SUBSTANCE ABUSE HISTORY

(For example: Denied -OR- None reported)

M5 — 405

SYMPTOMS

Think about the symptoms you've had over the past year, not just what you have today. The symptoms checked off below will determine which percentage the VA will assign to your mental disability. You will not have to have all symptoms checked off to get that percentage; however, the more the better.
(For example: You do not have to have all symptoms valued at 70% checked off in order to get awarded 70%, but the more symptoms you have valued at 70%, the better your chances. You will also need to have symptoms valued at 50% and 30% as well.)

M6 — Symptoms Valued at 100% 406

| | |
|---|---|
| M7 | Gross impairment in thought processes or communication 407 |
| M8 | Persistent delusions or hallucinations 408 |
| M9 | Grossly inappropriate behavior 409 |
| M10 | Persistent danger of hurting self or others 410 |
| M11 | Intermittent inability to perform activities of daily living, such as maintenance of minimal personal hygiene 411 |
| M12 | Disorientation to time or place |
| | Memory loss for names of close relatives, own occupation, or own name 412 |

Describe the symptoms you checked off:

M13 — 413

M14 — Symptoms Valued at 70% 414

| | |
|---|---|
| M15 | Suicidal ideation 415 |
| M16 | Obsessional rituals which interfere with routine activities 416 |
| M17 | Speech intermittently illogical, obscure, or irrelevant 417 |
| M18 | Near continuous depression and/or panic affecting the ability to function independently, appropriately, and effectively 418 |
| M19 | Difficulty adapting to stressful circumstances, including work or work-like settings 419 |
| M20 | Impaired impulse control, such as unprovoked irritability with periods of violence |
| | Spatial disorientation 420 |

VBA-MDBQ-2019-01 — 460

FIG. 4B

| | |
|---|---|
| M21 | Neglect of personal appearance and hygiene /421 |
| M22 | Inability to establish and maintain effective relationships /422 |

M23 — Describe the symptoms you checked off:

[423]

M24 — Symptoms Valued at 50%

| | |
|---|---|
| M25 | Flattened affect (no enjoyment in doing things you used to enjoy doing) /424 |
| M26 | Circumstantial, circumlocutory, or stereotyped speech /425 |
| M27 | Panic attacks more than once a week /426 |
| M28 | Difficulty in understanding complex commands /427 |
| M29 | Impairment of short- and long-term memory, retaining only highly learned material and forgetting to complete tasks /428 |
| M30 | Impaired judgement /429 |
| M31 | Impaired abstract thinking /430 |
| M32 | Disturbances of motivation and mood /431 |
| | Difficulty in establishing and maintaining effective work and/or social relationships /432 |

M33 — Describe the symptoms you checked off:

[433]

M34 — Symptoms Valued at 30%

| | |
|---|---|
| M35 | Anxiety /434 |
| M36 | Chronic sleep impairment (including nightmares) /435 |
| M37 | Mild memory loss, to include forgetting directions, names, and/or recent events or activities /436 |
| M38 | Depressed mood /437 |
| M39 | Suspiciousness /438 |
| | Panic attacks (weekly or less often) /439 |

M40 — Describe the symptoms you checked off:

[440]

VBA-MDBQ-2019-01 /460

FIG. 4C

OCCUPATIONAL AND SOCIAL IMPAIRMENT

Please select the option that most accurately describes how the mental disability affects your work and social relationships:

| | |
|---|---|
| M42 | My mental disability only causes mild symptoms, which does not interfere with my work and/or social life -10% — 441 |
| M43 | My mental disability occasionally causes mild-to-moderate symptoms, which can interfere with my work and/or social life -30% — 442 |
| M44 | My mental disability causes moderate symptoms, which frequently interfere with my work and/or social life -50% — 443 |
| M45 | My mental disability causes moderate-to-severe symptoms, which consistently interfere and obstruct my work and/or social life -70% — 444 |
| | My mental disability causes permanent interference in all areas of my life, which prevent me from living a normal life -100% — 445 |

(M41 labels the question block)

446

I CERTIFY THAT the information on this form is true and correct to the best of my knowledge and belief.

| PRINTED NAME: | | SIGNATURE: | |
|---|---|---|---|
| DATE: | | EMAIL ADDRESS: | |

447     460     M46     M47     448     M48
VBA-MDBQ-2019-01

VETERAN NAME: [ ]  VETERAN SSN: [ ]

FOR PHYSICIAN USE ONLY – PATIENT SHOULD NOT COMPLETE THIS FORM

VETERAN BENEFITS ADVANTAGE
Patient Evaluation Survey

Post-Traumatic Stress Disorder (PTSD)

PRE-EVALUATION NOTES TO THE PHYSICIAN
(Any notes that Veteran Benefits Advantage wants to address to the physician completing this survey will be here.)

503 — P3

CLINICAL FINDINGS
Please complete the following sections by asking the Veteran how the symptoms of PTSD have affected him or her. Only include information about situations and/or events that occurred during or after the Veteran's active duty military service. It is important that situations and/or events prior to active duty service be excluded.

RELEVANT SOCIAL/MARITAL/FAMILY HISTORY

504 — P4

RELEVANT OCCUPATIONAL AND EDUCATIONAL HISTORY

505 — P5

RELEVANT MENTAL HEALTH HISTORY
TO INCLUDE PRESCRIBED MEDICATIONS AND FAMILY MENTAL HEALTH

506 — P6

VBA-PES-2019-01 — 574

FIG. 5A

507   P7           ⸺ 500            508      P8
VETERAN NAME: [                    ]    VETERAN SSN: [    ]

RELEVANT LEGAL AND BEHAVIORAL HISTORY

P9 — 509

RELEVANT SUBSTANCE ABUSE HISTORY

P10 — 510

PTSD DIAGNOSTIC CRITERIA

CRITERION B:
The traumatic event is persistently re-experienced in 1 or more of the following ways:

P11 — ☐ Recurrent and distressing recollections of the event, including images, thoughts, or perceptions. — 511

P12 — ☐ Recurrent distressing dreams of the event. — 512

P13 — ☐ Acting or feeling as if the traumatic event were recurring. This includes a sense of reliving the experience, illusions, hallucinations and dissociative flashback episodes, including those that occur on awakening or when intoxicated. — 513

P14 — ☐ Intense psychological distress at exposure to internal or external cues that symbolize or resemble an aspect of the traumatic event. — 514

P15 — ☐ Physiological reactivity on exposure to internal or external cues that symbolize or resemble an aspect of the traumatic event. — 515

CRITERION C:
Persistent avoidance of stimuli associated with the trauma and numbing of general responsiveness (not present before the trauma), as indicated by 3 or more of the following:

P16 — ☐ Efforts to avoid thoughts, feelings, or conversations associated with the trauma. — 516

P17 — ☐ Efforts to avoid activities, places or people that arouse recollections of the trauma. — 517

P18 — ☐ Inability to recall an important aspect of the trauma. — 518

P19 — ☐ Markedly diminished interest or participation in significant activities. — 519

VBA-PES-2019-01 — 574

FIG. 5B

VETERAN NAME: [520 / P20]          VETERAN SSN: [521 / P21]

- ☐ Feeling of detachment or estrangement from others. —522
- ☐ Restricted range of affection (e.g., unable to have loving feelings). —523
- ☐ Sense of a foreshortened future (e.g., does not expect to have a career, marriage, children, or a normal life span). —524

CRITERION D:
Persistent symptoms of increased arousal, not present before the trauma, as indicated by 2 or more of the following:

- ☐ Difficulty falling or staying asleep. —525
- ☐ Irritability or outbursts of anger. —526
- ☐ Difficulty concentrating. —527
- ☐ Hypervigilence. —528
- ☐ Exaggerated startled response. —529

SYMPTOMS

Please check all symptoms that apply to the Veteran's diagnosis(es):

- ☐ Gross impairment in thought processes or communication —530
- ☐ Persistent delusions or hallucinations —531
- ☐ Grossly inappropriate behavior —532
- ☐ Persistent danger of hurting self or others —533
- ☐ Intermittent ability to perform activities of daily living, including maintenance of minimal personal hygiene —534
- ☐ Disorientation to time or place —535
- ☐ Memory loss for names of close relatives, own occupation, or own name —536
- ☐ Suicidal Ideation —537
- ☐ Obsessional rituals which interfere with routine activities —538
- ☐ Speech intermittently illogical, obscure, or irrelevant —539
- ☐ Near-continuous panic and/or depression affecting the ability to function independently, appropriately, and effectively —540
- ☐ Impaired impulse control such as unprovoked irritability with periods of violence —541
- ☐ Spatial disorientation —542

VBA-PES-2019-01 —574

FIG. 5C

VETERAN NAME: [543] (P43) [500]   VETERAN SSN: [544] (P44)

- P45 ☐ Neglect of personal appearance and hygiene  545
- P46 ☐ Difficulty adapting to stressful circumstances including work or a work-like setting  546
- P47 ☐ Inability to establish and maintain effective relationships  547
- P48 ☐ Flattened affect  548
- P49 ☐ Circumstantial, circumlocutory, or stereotyped speech  549
- P50 ☐ Panic attacks more than once a week  550
- P51 ☐ Difficulty in understanding complex commands  551
- P52 ☐ Impairment of short and long-term memory such as retention of only highly learned material and forgetting to complete tasks  552
- P53 ☐ Impaired judgement  553
- P54 ☐ Impaired abstract thinking  554
- P55 ☐ Disturbances of motivation and mood  555
- P56 ☐ Difficulty in establishing and maintaining effective work and/or social relationships  556
- P57 ☐ Anxiety  557
- P58 ☐ Chronic sleep impairment, including nightmares  558
- P59 ☐ Depressed mood  559
- P60 ☐ Mild memory loss such as forgetting names, forgetting directions, and forgetting recent events  560
- P61 ☐ Suspiciousness  561
- P62 ☐ Panic attacks, weekly or less often  562

| OCCUPATIONAL AND SOCIAL IMPAIRMENT |
|---|
| Which of the following best summarizes the Veteran's level of occupational and social impairment with regards to the mental diagnosis? (*Check only one*) |
| P63 ☐ Occupational and social impairment due to mild or transient symptoms which decrease work efficiency and ability to perform occupational tasks only during periods of significant stress, or symptoms controlled by medication.  563 |
| P64 ☐ Occupational and social impairment with occasional decrease in work efficiency and intermittent periods of inability to perform occupational tasks, although generally functioning satisfactorily, with normal routine behavior, self-care, and conversation.  564 |
| P65 ☐ Occupational and social impairment with reduced reliability and productivity.  565 |

VBA-PES-2019-01  574

VETERAN NAME: VETERAN SSN:

P68 — Occupational and social impairment with deficiencies in most areas, such as work, school, family relations, judgment, thinking, and/or mood. — 568

P69 — Total occupational and social impairment. — 569

OTHER SYMPTOMS

Does the Veteran have any other symptoms attributable to PTSD (and other mental disorders) that are not listed above?

P70 ◇ Yes    P71 ◇ No    570/571

P72 — If yes, describe:
572

ADDITIONAL COMMENTS

P73 —
573

VBA-FES-2019-01 — 574

PATIENT/VETERAN'S SOCIAL SECURITY NO. [682] [683] [684] (D82, D83, D84)

SECTION VI - PTSD DIAGNOSTIC CRITERIA

NOTE: Please check criteria used for establishing the current PTSD diagnosis. The diagnostic criteria for PTSD, referred to as Criteria A-F, are from the Diagnostic and Statistical Manual of Mental Disorders, 4th edition (DSM-IV).

D85 — CRITERION A: The Veteran has been exposed to a traumatic event where both of the following were present:
- D86 ☐ The Veteran experienced, witnessed or was confronted with an event that involved actual or threatened death or serious injury, or a threat to the physical integrity of self or others. — 685
- D87 ☐ The Veteran's response involved intense fear, helplessness or horror. — 686
- ☐ No exposure to a traumatic event. — 687

D88 — CRITERION B: The traumatic event is persistently re-experienced in 1 or more of the following ways:
- D89 ☐ Recurrent and distressing recollections of the event, including images, thoughts or perceptions. — 688
- D90 ☐ Recurrent distressing dreams of the event. — 689
- D91 ☐ Acting or feeling as if the traumatic event were recurring; this includes a sense of reliving the experience, illusions, hallucinations and dissociative flashback episodes, including those that occur on awakening or when intoxicated. — 690
- D92 ☐ Intense psychological distress at exposure to internal or external cues that symbolize or resemble an aspect of the traumatic event. — 691
- D93 ☐ Physiological reactivity on exposure to internal or external cues that symbolize or resemble an aspect of the traumatic event. — 692
- ☐ The traumatic event is not persistently re-experienced. — 693

D94 — CRITERION C: Persistent avoidance of stimuli associated with the trauma and numbing of general responsiveness (not present before the trauma), as indicated by 3 or more of the following:
- D95 ☐ Efforts to avoid thoughts, feelings or conversations associated with the trauma. — 694
- D96 ☐ Efforts to avoid activities, places or people that arouse recollections of the trauma. — 695
- D97 ☐ Inability to recall an important aspect of the trauma. — 696
- D98 ☐ Markedly diminished interest or participation in significant activities. — 697
- D99 ☐ Feeling of detachment or estrangement from others. — 698
- D100 ☐ Restricted range of affection (e.g., unable to have loving feelings). — 699
- D101 ☐ Sense of a foreshortened future (e.g., does not expect to have a career, marriage, children or a normal life span). — 700
- ☐ No persistent avoidance of stimuli associated with the trauma or numbing of general responsiveness. — 701

D102 — CRITERION D: Persistent symptoms of increased arousal, not present before the trauma, as indicated by 2 or more of the following:
- D103 ☐ Difficulty falling or staying asleep. — 702
- D104 ☐ Irritability or outbursts of anger. — 703
- D105 ☐ Difficulty concentrating. — 704
- D106 ☐ Hypervigilance. — 705
- D107 ☐ Exaggerated startle response. — 706
- ☐ No persistent symptoms of increased arousal. — 707

D108 — CRITERION E: Duration of symptoms:
- D109 ☐ The duration of the symptoms described in Criteria B, C and D is more than 1 month. — 708
- D110 ☐ The duration of the symptoms described in Criteria B, C and D is less than 1 month. — 709
- ☐ Veteran does not meet full criteria for PTSD. — 710

D111 — CRITERION F: Clinically significant distress or impairment:
- D112 ☐ The PTSD symptoms described above cause clinically significant distress or impairment in social, occupational, or other important areas of functioning. — 711
- D113 ☐ The PTSD symptoms described above do NOT cause clinically significant distress or impairment in social, occupational, or other important areas of functioning. — 712
- ☐ Veteran does not meet full criteria for PTSD. — 713

VA FORM 21-0960P-3, MAY 2013 — 764

Client List

| CASE STATUS 1 | CASE STATUS 2 | CASE STATUS 3 | CASE STATUS 4 |
|---|---|---|---|
| 354 Clients | 577 Clients | 239 Clients | 354 Clients |
| Oldest case: Jan 01, 2019 | Oldest case: Feb 01, 2019 | Oldest case: Feb 28, 2019 | Oldest case: Mar 01, 2019 |

― 770

NEEDS REVIEW — 771

« 1 2 3 » »

| NAME AND ID | NOTES | | | LAST UPDATE ∨ |
|---|---|---|---|---|
| John Doe #12332 | Lorem ipsum dolor sit amet, consectetur adipiscing elit. Fusce dapibus urna mauris, sit amet pulvinar... | | | 01/01/2019 |
| Opi Watihana #12332 | Lorem ipsum dolor sit amet, consectetur adipiscing elit. Fusce dapibus urna mauris, sit amet pulvinar... | | | 01/01/2019 |
| Lungelo Ngcaba #12332 | Lorem ipsum dolor sit amet, consectetur adipiscing elit. Fusce dapibus urna mauris, sit amet pulvinar... | | | 01/01/2019 |

ALL CLIENT LIST — 772

🔍 Search       State: All ∨    City: All ∨    Disability: All ∨    Status: All ∨

| NAME AND ID | STATE ∨ | CITY ∨ | DISABILITIES ∨ | DURATION ∨ | # DAYS ∨ | STATUS ∨ |
|---|---|---|---|---|---|---|
| John Doe #12332 | CA | Los Angeles | Arm, Back, Neck... | 3 Days | 40 | Case Status |
| Carmelita Marsham #12011 | IL | Chicago | Shoulder, Knee... | 4 Days | 38 | Case Status |

FIG. 7A

← Client List

John Doe — 775

STATUS: Doctor Review  ASSIGNED: James Cooper  Days Open: 12 — 776

33%
POTENTIAL INCREASE
CURRENT RATING 42.50%
POTENTIAL RATING 56.55% — 777

CLIENT INFO — 778
CLIENT ID: #12016  STATE: CA  CITY: Los Angeles
PHONE: +144-3412-4422  EMAIL: daijian@myemailservice.com  SOCIAL: ----1234

CLIENT DISABILITY: REE Medical/DBQ Review/SpaKinect; Platinum Medical Evaluations (PME- formerly HouseCall MD) Edit

| DISABILITY | TO BE EVAL | CURRENT RTG | POTENTIAL RTG | CLIENT MINI | DR. PES | FULL DBQ | LATEST UPDATE |
|---|---|---|---|---|---|---|---|
| BACK | ● To Be Evaluated | 0% | 20% | REVIEW | REVIEW | REVIEW | 04/30/2019 |
| NECK | ● To Be Evaluated | 0% | 20% | REVIEW | REVIEW | REVIEW | 04/30/2019 |
| KNEES | ○ To Be Evaluated | 0% | 20% | REVIEW | REVIEW | REVIEW | 04/30/2019 |
| EYES | ● To Be Evaluated | 0% | 20% | View | View | View | 03/31/2019 |

Download All DBQs

CASE HISTORY — 780
Case is assigned to Underwriter
Client completed Mini DBQ
Case is assigned to Doctor
Doctor completed PES
QC has claimed the case
QC returned the case to Doctor
Case is sent back to QC
QC passed the case to Underwriter
Underwriter completed reviewing case

CLIENT NOTES
Imperdiet dui accumsan sit amet nulla facilisi morbi tempus iaculis.

This is the content of a note. The user can add these notes to the DBQ.

FIG. 7B

Client List  354 Total Clients

NEEDS REVIEW

| NAME AND ID | NOTES | LAST UPDATE |
|---|---|---|
| John Doe #12332 | Lorem ipsum dolor sit amet, consectetur adipiscing elit. Fusce dapibus urna mauris, sit amet pulvinar... | 01/01/2019 |
| Opi Watihana #12332 | Lorem ipsum dolor sit amet, consectetur adipiscing elit. Fusce dapibus urna mauris, sit amet pulvinar... | 01/01/2019 |
| Lungelo Ngcaba #12332 | Lorem ipsum dolor sit amet, consectetur adipiscing elit. Fusce dapibus urna mauris, sit amet pulvinar... | 01/01/2019 |

ALL CLIENT LIST

Search | State: All ∨ | City: All ∨ | Disability: All ∨ | Status: All ∨

| NAME AND ID | STATE ∨ | CITY ∨ | DURATION ∨ | DISABILITIES ∨ | # DAYS ∨ | STATUS ∨ |
|---|---|---|---|---|---|---|
| John Doe #12332 | CA | Los Angeles | 3 Days | Arm, Back, Neck... | 40 | Case Status |
| Carmelita Mansham #12011 | IL | Chicago | 4 Days | Shoulder, Knee... | 38 | Case Status |
| Yasaman Faroutan #12012 | AZ | Phoenix | 16 Days | Ankle, Knee, Wrist | 16 | Case Status |
| Debashis Bhuiyan #12013 | CA | San Diego | 1 Day | Back | 12 | Case Status |
| Malin Quist #12014 | TX | Houston | 16 Days | Foot, Headache... | 33 | Case Status |

SYSTEMS AND METHODS FOR CONVERTING HUMAN INTERACTIONS TO POPULATE AN ELECTRONIC FORM

CROSS-REFERENCE TO RELATED APPLICATIONS

This application claims priority to U.S. Provisional Patent App. No. 62/736,381, filed on Sep. 25, 2018 and titled "SYSTEMS AND METHODS FOR COMPLETING AN ELECTRONIC FORM," the disclosure of which is incorporated herein in its entirety by reference.

BACKGROUND

Technical Field

Various embodiments described herein relate generally to the field of electronic management of information, and more particularly management of client information for auto-populating information on to electronic forms or documents.

Related Art

The following description includes information that may be useful in understanding the present invention. It is not an admission that any of the information provided herein is prior art or relevant to the presently claimed invention, or that any publication specifically or implicitly referenced is prior art.

Existing forms that must be completed and evaluated by various approval agencies/entities in order to obtain a specific result or benefit are difficult and time consuming for users to complete. The difficulty in completing forms often leads to users not completing the forms correctly or completely, which in turn results in the user not obtaining the correct results or benefits, and the evaluator not granting the benefits requested.

A few industries in which the above problems exist include healthcare (e.g., patient questionnaires, insurance forms), police departments (e.g., police reports, violations), insurance (e.g., customer claims, internal processing of forms), internal business needs (e.g., health benefits for employees, forms completed by employees relating to complaints, claims, surveys, etc.), financial industries (e.g., mortgage lending, banking), and real estate. Of course, it should be appreciated that the inventive subject matter could benefit any other industry in which long, tedious or complex forms are completed by internal staff, vendors, or customers.

Another field where the above problems have been found is in the area of disability benefits. A Veteran ("Vet") must submit a compensation claim ("claim") to the Department of Veterans Affairs ("VA") in order to be deemed to be service-connected ("SC"). When a compensation claim is related to a disability resulting from the Vet's military service, the Vet obtains monetary compensation according to their Disability Rating ("DR"). The VA renders a Rating Decision ("RD") for every claim a Vet submits. If a disability is deemed SC, then a rating percentage is assigned to that individual disability. The sum of all SC disabilities determines the Vet's overall DR.

Each disability that is deemed SC is given a rating percentage ("rating") based on a schedule outlined in the Electronic Code of Federal Regulations ("eCFR"), Title 38, Chapter 1, Part 4. The eCFR bases its schedule on the severity of a disability's symptoms. Each disability has its own schedule and potential ratings.

The VA has created medical forms entitled Disability Benefits Questionnaire ("DBQ") for every disability. Although DBQs can range from 2-11 pages, the average DBQ is 10 pages. The VA has released over 70 DBQs for public use. The purpose of Compensation & Pension ("C&P") exams is for examining physicians to complete DBQs to be used in the RD. A Vet often does not receive the benefits to which they are entitled in the RD due to errors in the C&P exam process. Based on the errors observed, it can be inferred that the majority of Vets do not have an accurate DR. A Vet on average needs 3-5 DBQs each for their claim, which could easily result in an RD of up to 50 pages in length.

The VA allows a Vet to submit DBQs completed by their medical providers. However, a Vet generally has to rely on C&P exams to obtain DBQs for their case. There are two main reasons for this: 1) a Vet may have a difficult time finding doctors willing to fill out up to 50 pages of DBQs; and 2) VA raters typically do not use private DBQs because doctors generally do not know how to properly complete DBQs. Therefore, most private DBQs are deemed inadequate for rating purposes due to being incomplete or inconsistent with VA laws and regulations and the other SC disabilities. Furthermore, the VA examining doctors completing DBQs from C&P exams may provide only the minimum required information on the DBQ due to time constraints, which may result in a low rating for the Vet in the RD.

Thus, there is a need for improved systems and methods for completing and submitting complex forms and the present disclosure is directed toward overcoming one or more of the problems identified above and/or providing advantages over prior systems.

SUMMARY

A system for populating an electronic form is disclosed herein. The system comprises one or more databases, at least one user interface, and a platform server comprising at least one processor communicatively coupled to the one or more databases and the at least one user interface. The one or more databases store a plurality of original forms, a plurality of abbreviated forms each corresponding to an original form of the plurality of original forms, and a plurality of conversion rules each corresponding to an original form of the plurality of original forms. The at least one user interface is configured to receive data related to at least one abbreviated form, wherein the data is based on client inputs into fields of the at least one abbreviated form. The platform server is programmed to extract input data from the at least one abbreviated form based on the data related to the at least one abbreviated form, populate the original form based on the input data and conversion rules of the plurality of conversion rules corresponding to the original form to generate a completed original form, and transmit the completed original form to a client via the at least one user interface.

In another aspect, a method for populating an electronic form is disclosed herein. The method comprises extracting, by one or more processors coupled to one or more databases, input data from at least one abbreviated form based on data related to the at least one abbreviated form, the data being received based on client inputs into fields of the at least one abbreviated form, wherein the at least one abbreviated form corresponds to an original form of a plurality of original forms stored in the one or more databases. The method also includes populating, by the one or more processors, the original form using the input data and conversion rules of a plurality of conversion rules corresponding to the original form to generate a completed original form, and transmitting the completed original form to a client via the at least one user interface.

In another aspect, a system for auto-populating a Disability Benefits Questionnaire (DBQ) disclosed herein. The system comprises one or more databases, at least one user interface, and a platform server comprising at least one processor communicatively coupled to the one or more databases and the at least one user interface. The one or more databases store disability information related to a plurality of disabilities, a plurality of original DBQs each corresponding to a disability of the plurality of disabilities, a plurality of abbreviated DBQs each corresponding to a disability of the plurality of disabilities, and a plurality of conversion rules each corresponding to an original DBQ of the plurality of original DBQs. The at least one user interface is configured to receive inputs related to a disability. The platform server programmed to obtain, via the at least one user interface, data representative of a first disability of the plurality of disabilities and retrieve a first abbreviated DBQ of the plurality of abbreviated DBQs and a second abbreviated DBQ of the plurality of abbreviated DBQs based on the first disability represented by the obtained data. The platform server is also programmed to extract first input data representative of answers input into fields of the first abbreviated DBQ by a first end user and extract second input data representative of answers input into fields of the second abbreviated DBQ by a second end user. The platform server is further programmed to populate an original DBQ of the plurality of original DBQs based on the first input data and the second input data using conversion rules corresponding to the original DBQ to generate a completed original DBQ, wherein the original DBQ corresponds to the first disability and the first abbreviated DBQ and the second abbreviated DBQ are truncated versions of the original DBQ, and provide the completed original DBQ to the first end user via the at least one user interface.

Various objects, features, aspects and advantages of the embodiments disclosed herein will become more apparent from the following detailed description of preferred embodiments, along with the accompanying drawing figures in which like numerals represent like components.

BRIEF DESCRIPTION OF THE DRAWINGS

Various embodiments disclosed herein are described in detail with reference to the following figures, in which like reference numerals refer to like parts. The figures are provided for purposes of illustration only and merely depict typical or exemplary embodiments. These figures are provided to facilitate the reader's understanding and shall not be considered limiting of the breadth, scope, or applicability of the embodiments. It should be noted that for clarity and ease of illustration these drawings are not necessarily made to scale.

FIGS. 4A through 4D illustrate an example abbreviated form, according to the various embodiments disclosed herein;

FIGS. 5A through 5E illustrate another example abbreviated form, according to the various embodiments disclosed herein;

Figure 6A:
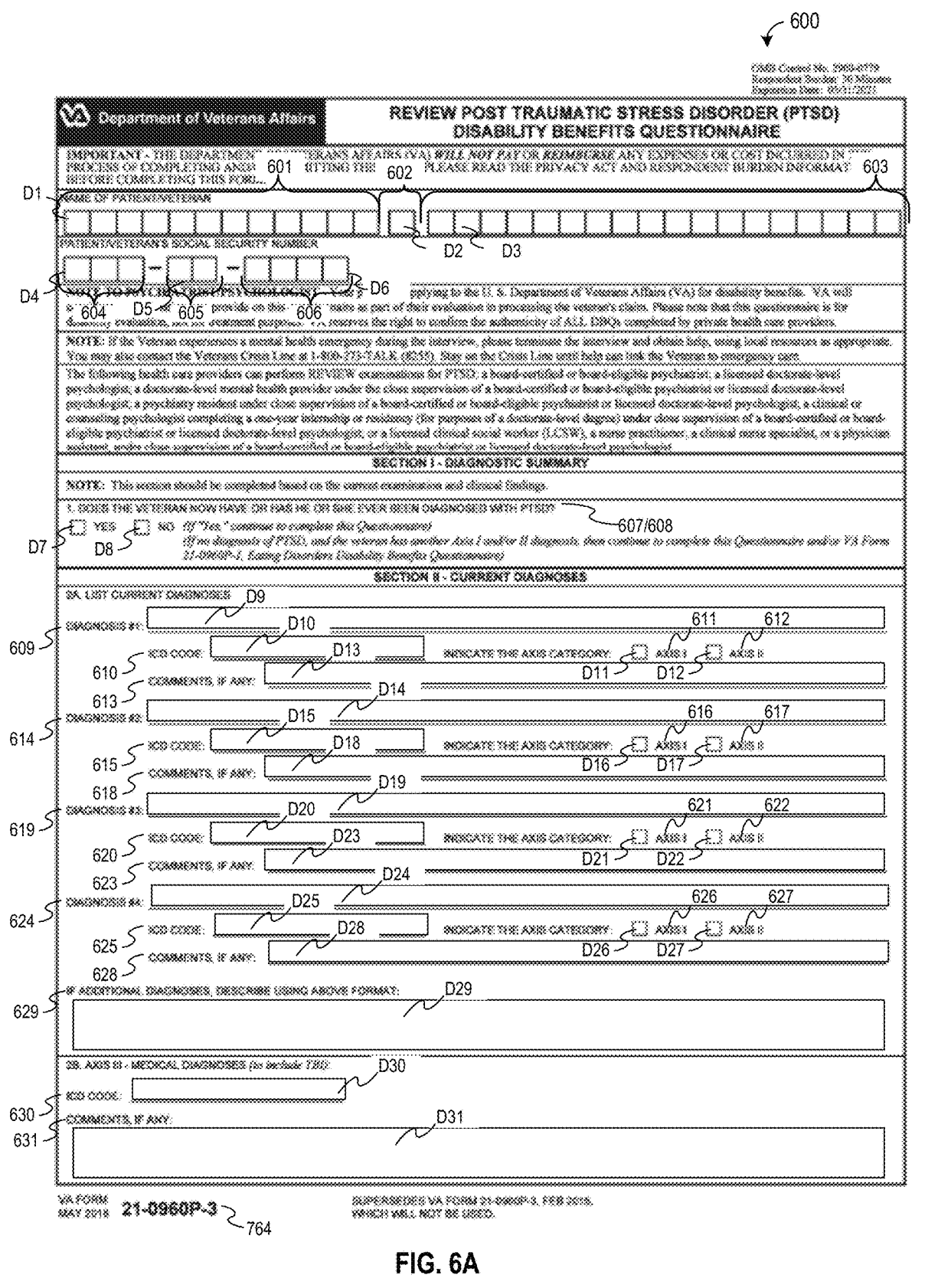
Figure 6B:
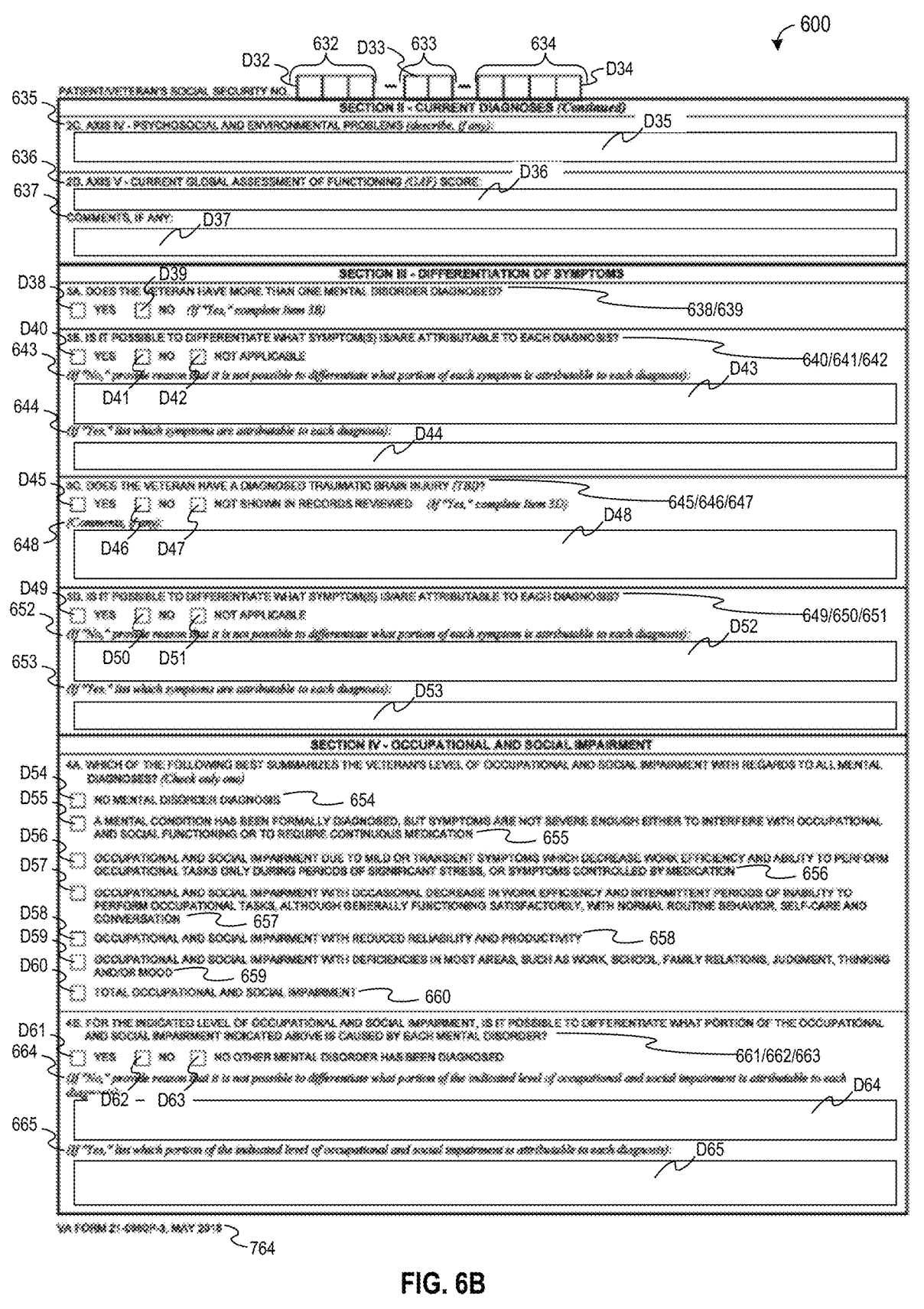
Figure 6C:
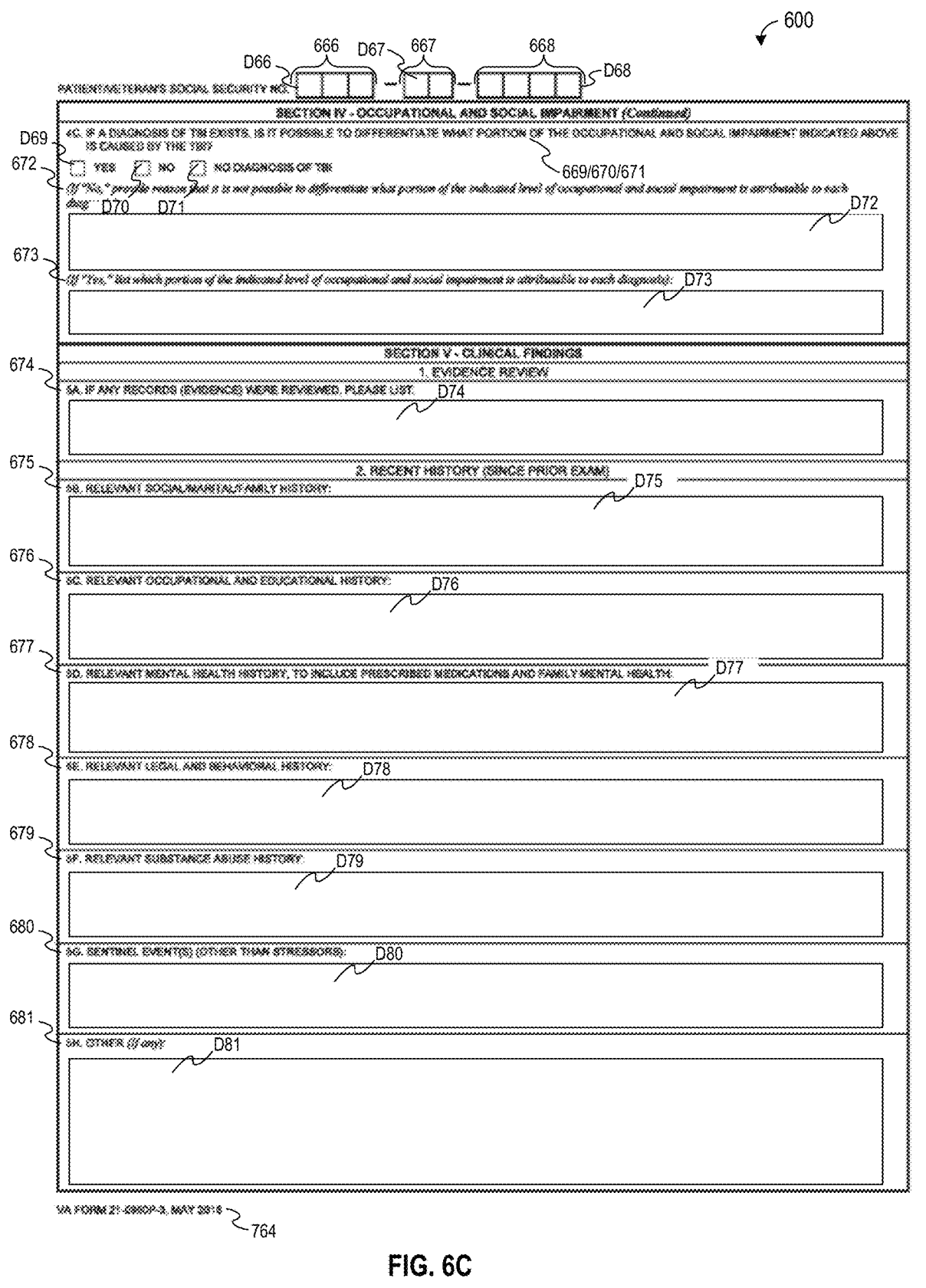
Figure 6E:
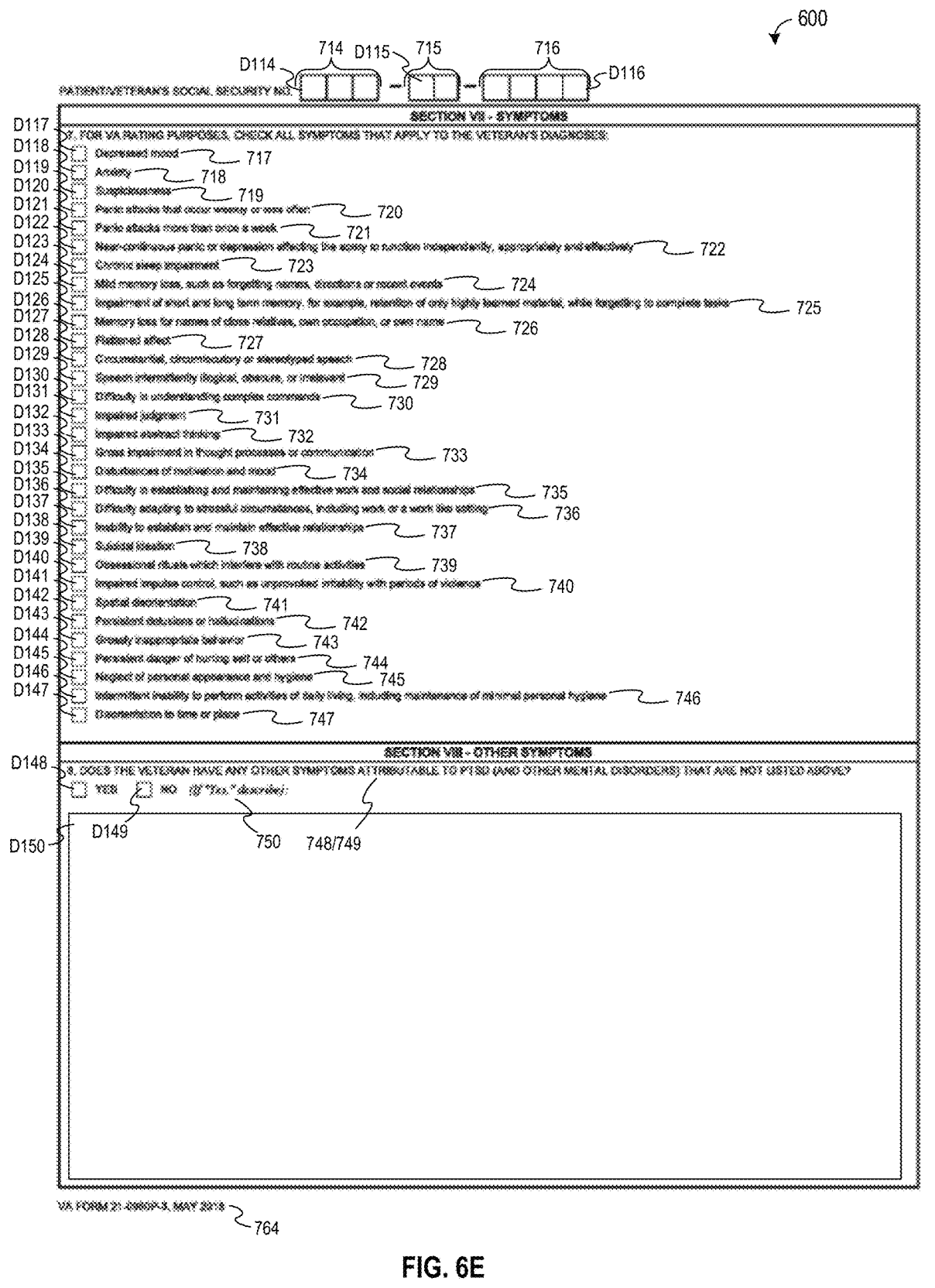
Figure 6F:
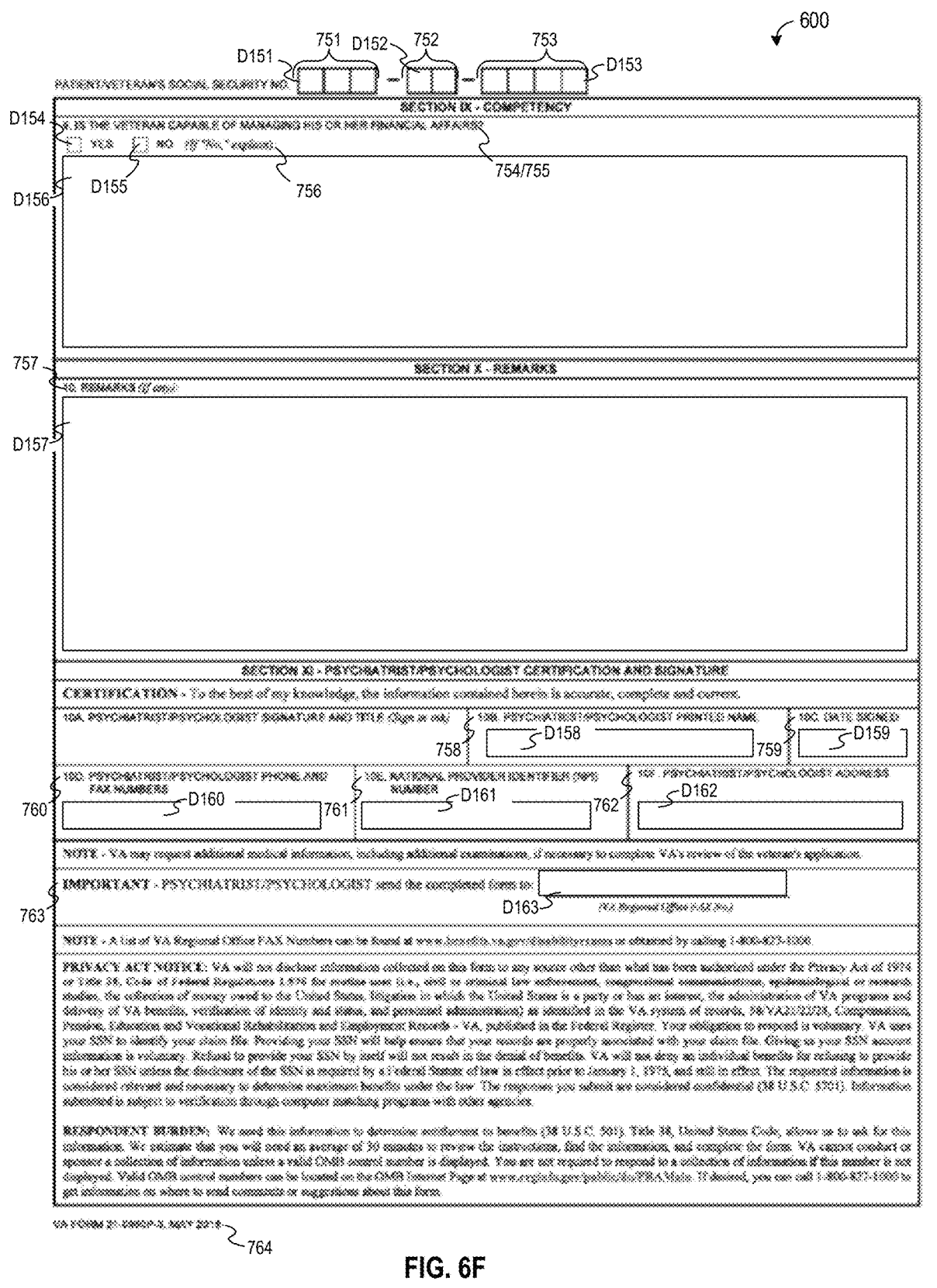

FIGS. 6A through 6F illustrate an example original form, according to the various embodiments disclosed herein;

FIGS. 7A through 7D illustrate example screens generated by the system of FIG. 2 and displayed on an end user device, according to the various embodiments disclosed herein.

DETAILED DESCRIPTION

Figure 1:
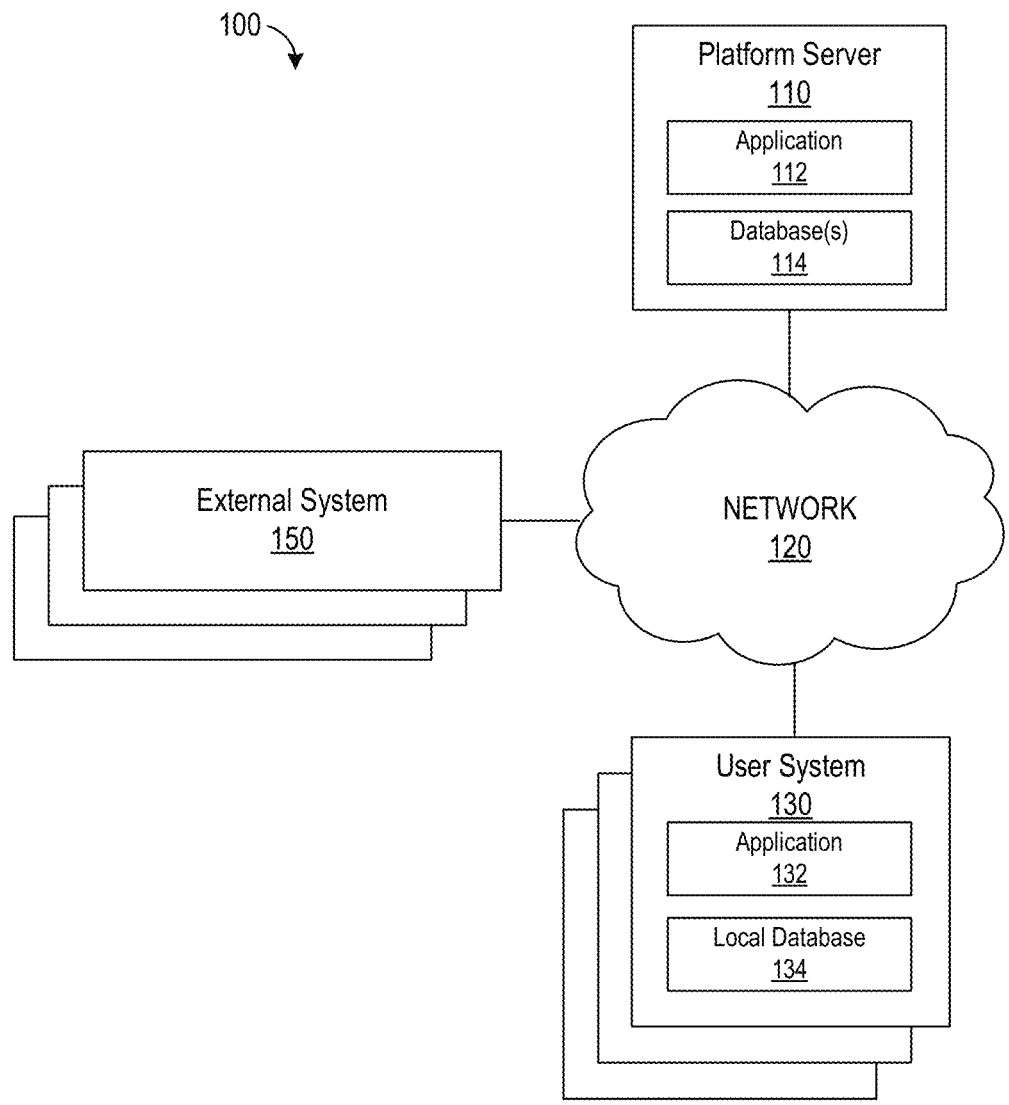
FIG. 1 schematically illustrates an example infrastructure in which the disclosed system may operate, according to the various embodiments disclosed herein.

The detailed description set forth below, in connection with the accompanying figures, is intended as a description of various embodiments and is not intended to represent the only embodiments in which the disclosure subject matter may be practiced. The detailed description includes specific details for the purpose of providing a thorough understanding of the embodiments. However, it will be apparent that those skilled in the art will be able to understand the disclosure without these specific details. In some instances, well-known structures and components are shown in simplified form for brevity of description. Some of the surfaces have been left out or exaggerated for clarity and ease of explanation.

The embodiments disclosed herein provide for systems and methods in which a client completes a shortened or otherwise modified questionnaire, form or other series of inquiries (referred to herein as an "abbreviated form") that is related to an original form (referred to herein as an "original form") provided or used by a third party for approving a decision based on the accurate completion of the original form (referred to herein as an "approving entity"). The abbreviated form may be a truncated version of the original form or may be created based on the original form so to be completed with all pertinent information necessary for completing the original from. In some aspects, the abbreviated form may be less than ⅒, less than ⅕, or even less than ⅓ of the complexity and/or length of the original form. It should be appreciated that the term "form" is used broadly to encompass, among other things, electronic forms (e.g., electronic forms, documents, or webpages as well as printable electronic forms and/or documents) or other questionnaires with blank spaces for information to be inserted or multiple choice questions, electronic or other surveys, and electronic or other multiple choice forms. Based on the client's submission, the client receives a fully completed and quality controlled original form to be submitted to the approving entity for review. In some aspects, contemplated systems may submit the quality controlled original form to the approving entity upon passing quality control, without further interactions by the client.

Embodiments described herein may map inputs and data (e.g., documents, text, audio, video, image, login information, etc.) in one or more abbreviated forms to a corresponding original form. For example, embodiments herein may present the client and/or user with related abbreviated forms, receive interactions (e.g., inputs) onto to the abbreviated forms, map data relating to the inputs on the abbreviated forms to the original form based on a set of conversion rules, and populate the original form using the mapping. Embodiments herein may also allow the client to interface with users of the systems described herein, for example an administrator, professional, or employee associated with the approval entity, and present completed original forms and data to the user. In some aspects, the systems and methods further facilitate the client's submission of the forms with the proper entity or entities.

The process may include creating abbreviated forms based on a determination as to what is critical and essential for the accurate completion of the form. The original form is analyzed to identify what is key and critical to accomplish the purpose of the form. The embodiments here synthesize the original form into an abbreviated or mini form to accomplish the objective of the original form's intent. Embodiments disclosed herein relate to systems and methods for facilitating accurate and quality controlled completion of long, tedious or complex forms for analysis and approval. In some aspects, a computer software application (sometimes referred to herein as "platform") is provided in which a user answers basic questions or queries (e.g., via inputs into fields of an abbreviated form provided via a device interface) and converts the answers using a corresponding set of rules to a completed original form for the user. The application or platform may be coupled to one or more databases or engines hosted on one or more servers that map inputs into fields on the abbreviated form to one or more fields in the original form. From a client's perspective, the client of contemplated systems could complete an abbreviated form associated with the original form, and receive a fully completed original form that is completed by the system based on inputs to the abbreviated form. Advantageously, the systems uses rules/logic (referred to herein as "conversion rules") associated with the abbreviated form and/or original form for completing the original forms based on user inputs so that the entity reviewing the original form will accept it.

The abbreviated version of the original document is put into an abbreviated format, which in turn allows it to be completed easily and timely. The inputs in the abbreviated form are then coded into a software application. The software application allows the abbreviated form to only input what is necessary to accomplish the original form's intent. An abbreviated form could be associated with any type of approving entity in any industry where completion of an original form is required. In some preferred aspects the abbreviated form is a simplified or shortened version of an original form determined by a substantive amount of data necessary to complete the original form's intended purpose. The answers provided by a client in response to the abbreviated form or questionnaire are sufficient to allow the system to complete the original form by allowing the client to focus solely on the original form's intended purpose. The abbreviated forms and the computer software applications disclosed herein allow users to "complete" original forms in much less time and with a greater degree of accuracy.

An example usage of the embodiments disclosed herein relates to the services of Veteran Advantage Enterprises ("VAE"), LLC. That is, examples provided herein are related to facilitating completion of DBQs for submission to the VA. In this scenario, the term "user" may refer to those administrators, professionals, and/or employees associated with the approval entity, for example but not limited to, case managers, underwriters, doctors, or any persons associated with the approval entity (e.g., the VA). The term "client" may refer to a person seeking to submit the form to the approval entity, for example, a Vet may be a client seeking to submit DBQs completed via embodiments disclosed herein.

Systems described herein may also be suitable for use in connection with original forms that comprise check boxes or multiple choice questions. However, it is contemplated that systems and methods disclosed herein could be used for various types of forms provided or reviewed by various types of approving entities. The examples described herein are generally focused on DBQs provided and reviewed by the Veterans Administration. While examples provided herein are described in connection with VAE applications, it will be appreciated that the disclosure is not limited to only VAE applications and can be made into an application to benefit numerous other industry forms used by any approving entity. For example, the systems described herein could be used by police officers in facilitation the completion of police reports. The abbreviated form stored in the abbreviated form database could comprise a shortened version of a police report (original form). As a non-limiting example of how the system could map a client's (e.g., the police officer's) inputs for completing an original form, the abbreviated form could require that the client enter a badge number, which the system could use to complete various sections in the original form (e.g., name, location, type of violation, unit). It is also contemplated that the system could also use information associated with the client login to complete certain portions of the original form without requiring additional user input.

Other contemplated industries in which embodiments disclosed herein could be used include healthcare (e.g., patient questionnaires, insurance forms), police departments (e.g., police reports, violations), insurance (e.g., customer claims, internal processing of forms), internal business needs (e.g., health benefits for employees, forms completed by employees relating to complaints, claims, surveys, etc.), banking and lending, and any other industry in which long, tedious or complex forms are completed by internal staff, vendors, or customers.

For example, embodiments disclosed herein could be used to assist large companies seeking to create self-carried health insurance programs and their employees in more easily completing complex health insurance forms. Health care facilities that require patients to complete initial intake questionnaires, insurance agencies needing complex forms completed, and government agencies requiring multiple forms to be filled out would each benefit from the systems described herein. Police officers frequently have to complete long tedious police reports, which the inventive subject matter could streamline.

FIG. 1 schematically illustrates an example infrastructure in which the disclosed system may operate, according to the various embodiments disclosed herein. The infrastructure may comprise a platform server 110 which hosts and/or executes one or more of the various functions, processes, and/or methods described herein. Platform server 110 may comprise one or more dedicated servers, or may instead comprise cloud instances, which utilize shared resources of one or more servers. These servers or cloud instances may be collocated and/or geographically distributed. Platform server 110 may also comprise or be communicatively connected to application 112 and/or one or more databases 114. In addition, platform server 110 may be communicatively connected to one or more user systems 130 via network 120. Platform server 110 may also be communicatively connected to one or more external systems 150 (e.g., websites, apps, other servers, etc.) via network 120. Platform server 110 may be implemented as one or more computing devices such as for example the computing device 800 illustrated in FIG. 8 discussed below.

Network 120 may include the Internet, and platform server 110 may communicate with user system(s) 130 through the Internet using standard transmission protocols, such as HyperText Transfer Protocol (HTTP), Secure HTTP (HTTPS), File Transfer Protocol (FTP), FTP Secure (FTPS), SSH FTP (SFTP), and the like. While platform server 110 is illustrated as connected to various systems through a single set of network(s) 120, it should be understood that platform server 110 may be connected to the various systems via different sets of one or more networks. For example, platform server 110 may be connected to a subset of user systems 130 and/or external systems 150 via the Internet, but may be connected to one or more other user systems 130 and/or external systems 150 via an intranet. Network 120 may also include any wired or wireless network, for example, a cellular network (e.g., 3G, 4G LTE, 5G, etc.), local area network (LAN), wide area network (WAN), etc. Furthermore, while only a few user systems 130, external systems 150, server application 112, and one set of database(s) 114 are illustrated, it should be understood that the infrastructure may comprise any number of user systems, server applications, and databases.

User system(s) 130 may comprise any type of computing devices capable of wired and/or wireless communication, including, without limitation, desktop computers, laptop computers, tablet computers, smart phones or other mobile phones, wearable mobile devices, servers, game consoles, televisions, set-top boxes, electronic kiosks, and the like. User system(s) 130 may be one or more computing devices such as for example the computing device 800 illustrated in FIG. 8 discussed below.

Platform server 110 may comprise web servers which host one or more websites, web services, and/or web-based applications. In embodiments in which a website is provided, the website may comprise one or more user interfaces, including, for example, webpages generated in HyperText Markup Language (HTML) or other language. Platform server 110 transmits or serves these user interfaces in response to requests from user system(s) 130. In some embodiments, these user interfaces may be served in the form of a wizard, in which case two or more user interfaces may be served in a sequential manner, and one or more of the sequential user interfaces may depend on an interaction of the user or user system 130 with one or more preceding user interfaces. The requests to platform server 110 and the responses from platform server 110, including the user interfaces, may both be communicated through network 120, which may include the Internet. These user interfaces or web pages may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases (e.g., database(s) 114) that are locally and/or remotely accessible to platform server 110. Platform server 110 may also respond to other requests from user system(s) 130.

Platform server 110 may further comprise, be communicatively coupled with, or otherwise have access to one or more database(s) 114. For example, platform server 110 may comprise one or more database servers which manage one or more databases 114. A user system 130 or server application 112 executing on platform server 110 may submit data (e.g., user data, form data, etc.) to be stored in database 114 and/or request access to data stored in database 114. Any suitable database may be utilized, including without limitation MySQL™, Oracle™ IBM™, Microsoft SQL™, Sybase™, Access™, and the like, including cloud-based database instances and proprietary databases. Data may be sent to platform server 110, for instance, using the well-known POST request supported by HTTP, via FTP, etc. This data, as well as other requests, may be handled, for example, by server-side web technology, such as a servlet or other software module (e.g., application 112), executed by platform server 110.

In embodiments in which a web service is provided, platform server 110 may receive requests from user systems 130 and/or external system(s) 150, and provide responses in eXtensible Markup Language (XML) and/or any other suitable or desired format. In such embodiments, platform server 110 may provide an application programming interface (API) which defines the manner in which user system(s) 130 and/or external system(s) 150 may interact with the web service. Thus, user system(s) 130 and/or external system(s) 150 (which may each themselves be servers) can define their own user interfaces and rely on the web service to implement or otherwise provide the backend processes, methods, functionality, storage, etc., described herein. For example, in such an embodiment, a client application 132 executing on one or more user system(s) 130 may interact with a server application 112 executing on platform server 110 to execute one or more or a portion of one or more of the various functions, processes, methods, and/or software modules described herein. Client application 132 may be "thin," in which case processing is primarily carried out server-side by server application 112 on platform server 110. A basic example of a thin client application is a browser application, which simply requests, receives, and renders webpages at user system(s) 130, while the server application on platform server 110 is responsible for generating the webpages and managing database functions. Alternatively, the client application may be "thick," in which case processing is primarily carried out client-side by user system(s) 130. It should be understood that client application 132 may perform an amount of processing, relative to server application 112 on platform server 110, at any point along this spectrum between "thin" and "thick," depending on the design goals of the particular implementation. In any case, the application described herein, which may wholly reside on either platform server 110 (e.g., in which case application 112 performs all processing) or user system(s) 130 (e.g., in which case application 132 performs all processing) or be distributed between platform server 110 and user system(s) 130 (e.g., in which case server application 112 and client application 132 both perform processing), can comprise one or more executable software modules that implement one or more of the processes, methods, or functions of the application(s) described herein.

Figure 2:
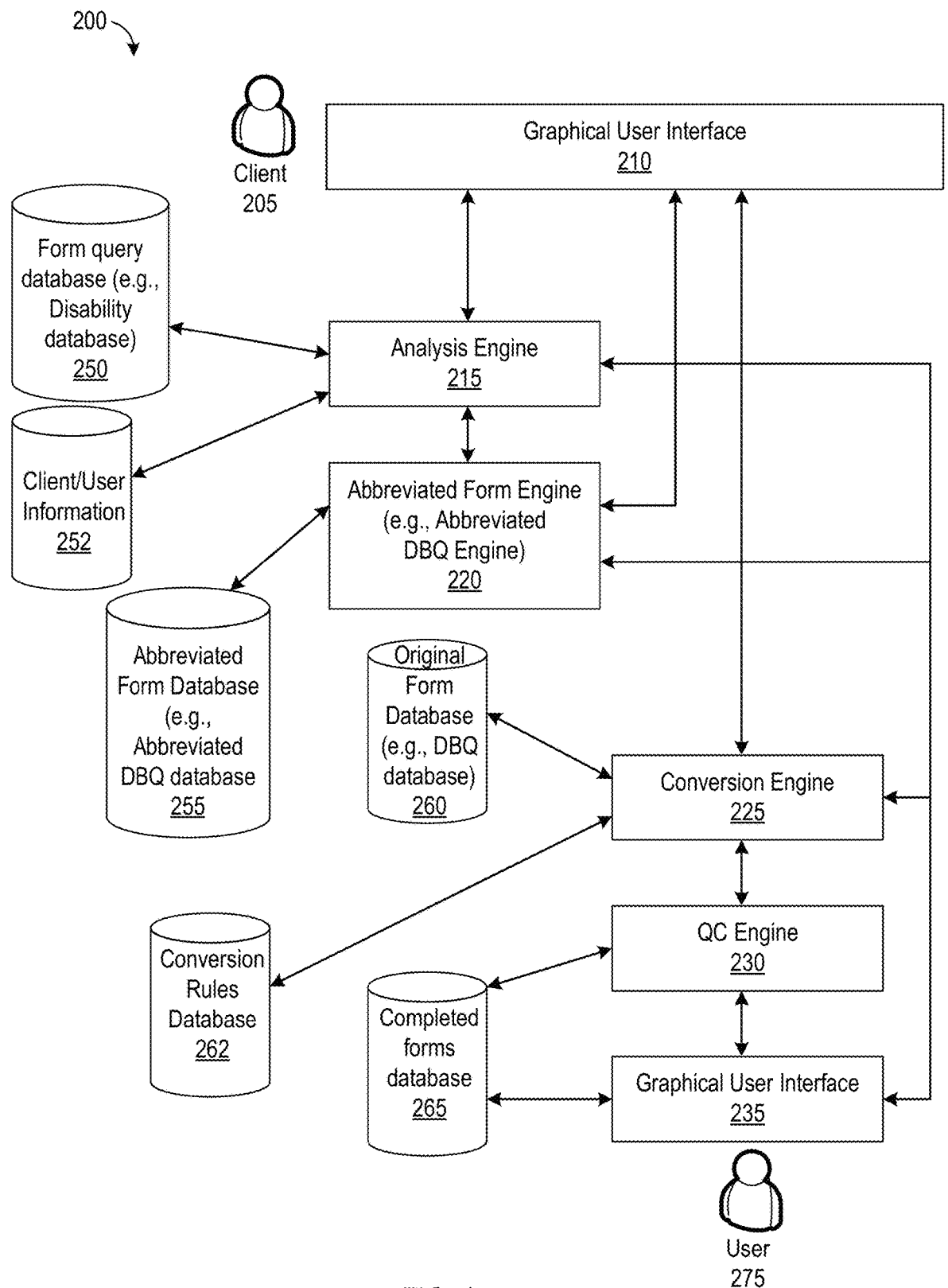
FIG. 2 schematically illustrates an example platform environment for use in completing an original form, according to the various embodiments disclosed herein.

FIG. 2 schematically illustrates an example platform environment for use in completing an original form, according to the various embodiments disclosed herein. The platform environment 200 may be a computing environment hosted by, for example, platform server 110 of FIG. 1, and may be executed thinly or thickly by application 112 and/or user application 132. For example, the platform environment 200 may generate graphical user interface 210 and graphical interface 235, either of which may be executed, for example, by a user application 132 functioning as a thin or thick client. The graphical user interface 210 may generate screens and other interfaces for receiving inputs based on client 205 interactions with the screens via input devices. Similarly, graphical user interface 210 may generate screens and other interfaces for receiving inputs from user 275 interactions with the screens via input devices.

Input data related to interactions received from client 205 via graphical user interface 210 and/or user 275 via graphical user interface 235 may be transmitted to one or more of an analysis engine 215, abbreviated form engine 220, conversion engine 225, and/or QC engine 230, each of which may be configured to execute one or more of the various functions, processes, and/or methods described herein. One or more of the various engines of FIG. 2 may be hosted by the platform server 110 and executed either locally at the platform server 110 or by a user system 130 communicatively coupled to the platform server 110.

The various engines may be communicatively coupled to one or more databases, for example but not limited to, a form query database 250, a client/user information database 252, an abbreviated form database 255, an original form database 260, and a completed forms database 265. Each database may store data that may be retrieved, accessed, extracted, derived, etc. during execution of the various functions, processes and methods described herein. The various databases of FIG. 2 may be implemented, for example, as one or more of database(s) 114, 132, and/or 142 based on the location of the respective database. For example, one or more databases may be hosted by the platform server 110 and would be included as one or more of database(s) 114.

The form query database 250 may provide storage for data for identifying original forms (e.g., form identifiers). For example, in the illustrative example, the form query database 250 may store identifiers as disabilities associated with original form names (e.g., representative of original DBQs). In some embodiments, the original form name may be descriptive to the original form or a non-descriptive, pseudo random identifier that is unique to each original form. Thus, the form query database 250 may store a plurality of identifiers (e.g., disabilities), each associated with a respective original form name of a plurality of original form names. The form query database 250 may also store a plurality of symptoms, one or more of which are associated with any given disabilities. In this way, symptoms may be used to identify respective disabilities, which may be used to retrieve an original form name.

Figure 3:
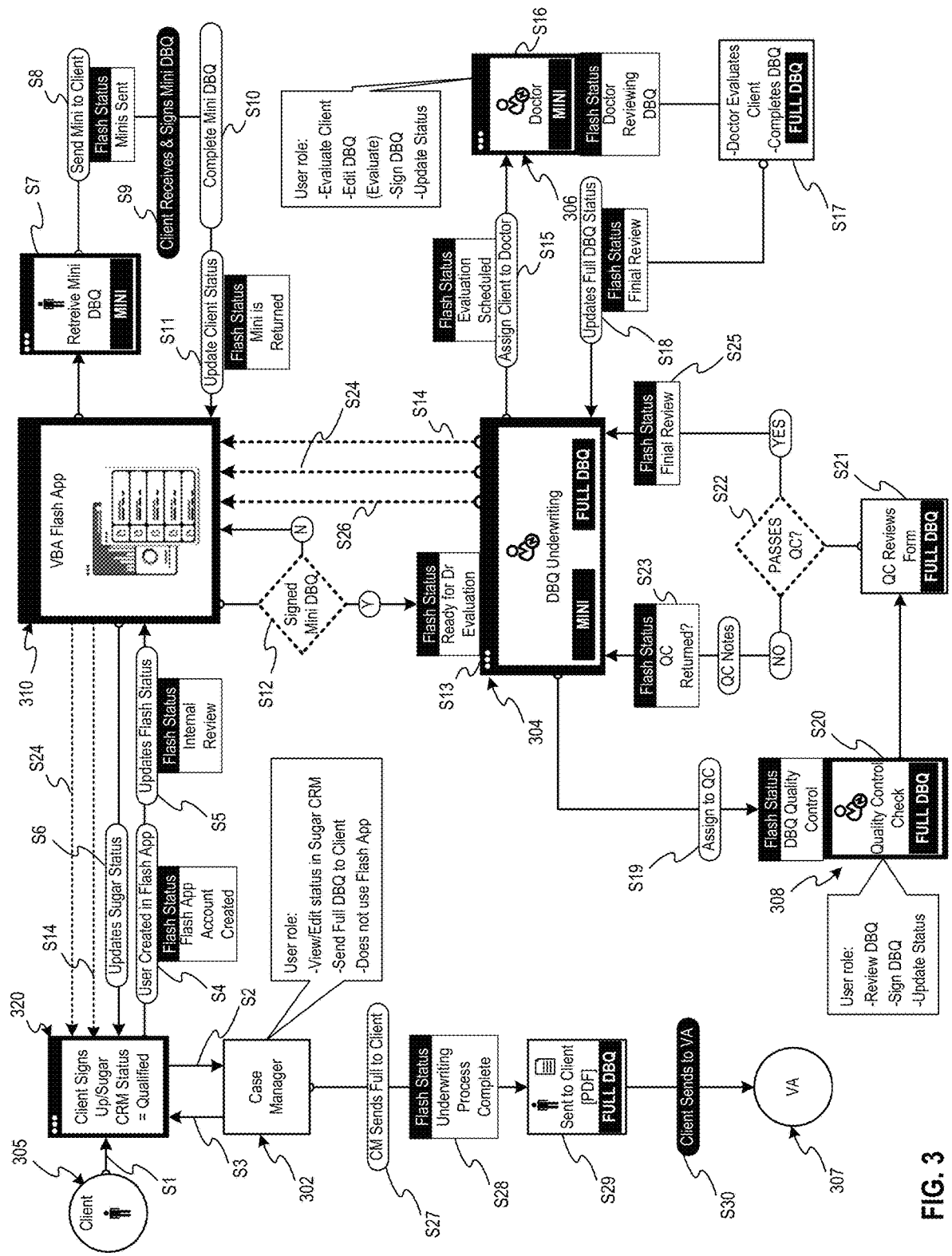
FIG. 3 illustrates an example process flow performed by the platform environment for completing an original form, according to the various embodiments disclosed herein.

The client/user information database 252 comprises user and client identification data, for example, data associated with the login credentials (e.g., usernames, passwords, biometrics), birthdates, social security numbers, contact information (e.g., addresses, emails, and phone numbers), client ID numbers, registration numbers indicative of a license to practice (e.g., credentials and/or clinic information), signature data, status identifiers (including status updates within the system as described below in detail in connection with FIG. 3), current and potential disability ratings (e.g., based on previously submitted original forms and to-be-completed original forms, respectively), and other pertinent client and/or user information. For example, the client/user information database 252 may also store data indicative of disabilities, for each client, that are eligible for potential rating increases. For example, as described above, for every disability associated with a given client, an abbreviated form is sent to the client to determine if the client should be evaluated. The platform environment 200 interprets the inputs the client provides on each abbreviated form, based on conversion rules and logic, to determine a potential rating for each disability is expected to receive from the VA. The potential rating values determine which disabilities will go forward to be evaluated by the doctor. If the results from the abbreviated form do not show an increase in potential rating is warranted, then that disability will not be evaluated by the doctor.

The abbreviated form database 255 may store a plurality of abbreviated forms in association with an abbreviated form locator. In some embodiments, a disability stored in the form query database 250 may be used as a locator, while in another embodiment the locator may be an original form name. Thus, each abbreviated form may be stored in association with one or more of the corresponding disability and the original form name. The abbreviated form database 255 may also store completed abbreviated forms and data representative of inputs thereon.

The original form database 260 may store a plurality of original forms in association with an original form locator. As with the abbreviated form database 255, the original form locator may be a disability and/or the original form name in the form query database 250.

The conversion rules database 262 may store a plurality of conversion rules, each corresponding to an abbreviated form of the abbreviated form database 255. The conversion rules may be stored in association with a rule locator, which may be one or more of an identifier of the abbreviated form, the disability corresponding to the abbreviate form, and the name of the original form. Thus, the platform environment 200 provides storage for the plurality of original forms, the plurality of abbreviated forms each corresponding and an original form of the plurality of original forms, and the plurality of conversion rules each corresponding to an abbreviated form.

The completed forms database 265 may store completed original forms generated by the platform environment 200.

The various functions, processes, and/or methods of FIG. 2 will be described illustratively for completing one or more forms (e.g., DBQs). However one skilled in the art will appreciated that the scope of the embodiments herein are not so limited and the embodiments herein are equally applicable to other applications where any complex form may be complete.

Client 205, a veteran or a person acting on behalf of the veteran in this example, may submit relevant documentation and inputs via interactions with the graphical user interface 210. As described above, graphical user interface 210 may be a means by which the client interacts with the platform environment 200 via a user system (e.g., user system 130 of FIG. 1), including the use of input devices such as a cell phone, tablet or computer, and software. The inputs can comprise any data, including images, videos, audio, text, or documents.

The graphical user interface 210 is communicatively coupled with an analysis engine 215. The analysis engine can be programmed to obtain and analyze the inputs (e.g., receive, extract, derive), extract data representative of the inputs (referred to herein as "input data"), and associate the input data with one or more disabilities via information stored in the form query database 250 or with one or more pieces of information associated with the client (e.g., login credentials, birthdate, social security number, address, or other client identifying information) in user/client information database 252. For example, inputs may include credentials for registering with the platform environment 200 and/or authenticating the client 205 via login credentials. The analysis engine may ingest these inputs and access the client/user information database 252 to identify and authenticate the client. In another example, the client 205 may input information related to one or more disabilities experienced by the client 205, which the analysis engine 215 ingests to identify disabilities in the form query database 250 and retrieve a form identifier associated with the disability in the form query database 250. Inputs may include any forms of data, including Word, PDF, and Excel documents, text, images, audio, and video.

Once the analysis engine 215 associates the inputs with one or more disabilities and retrieves the form identifier, analysis engine 215 forwards the form identifier to the abbreviated form engine 220 as an abbreviated form locator, which accesses the abbreviated form database 255 to locate and retrieve one or more abbreviated forms corresponding to the abbreviated form locator (e.g., corresponding to the identifier original form and/or disability). As noted above, the abbreviated form database 255 stores the abbreviated forms in association with corresponding disabilities and/or form identifiers that may be referenced in form query database 250.

The analysis engine 215 or the abbreviated form engine 220 may then generate and display the retrieved abbreviated forms onto a user system of the client 205. An example of an abbreviated form is illustrated in FIGS. 4A through 4D, which illustrate an example abbreviated DBQ for a given disability. In various embodiments, the client may be sent an online link to complete the abbreviated form. For example, a message in the form of an email, text message (e.g., short messaging services (SMS), multimedia messaging services (MMS), rich communication services (RCS), etc.), or similar messaging service may be forwarded to the client 205 with a link to the abbreviated DBQ. The abbreviated DBQ may be downloaded, printed, or completed as a web-based form. In another embodiment, an electronic copy of the abbreviated DBQ may be included in the message (e.g., as a PDF or other electronic form). The client 205 may access the link or attached electronic copy, which opens up the abbreviated DBQ to which the client 205 can interact to input answers to a few (e.g., 2-20, 2-15, 10-15, 5-15, 3-10, 3-7) questions. The questions may be displayed on the graphical user interface 210 in a format of an abbreviated DBQ.

In some embodiments, the analysis engine 215 or abbreviated form engine 220 may identify a plurality of corresponding abbreviated forms. For example, inputs from the client 205 may correspond to a plurality of disabilities, each associated with one or more different abbreviated forms. The analysis engine 215 or abbreviated form engine 220 may provide access to each abbreviated form in a single message or in separate messages and the client 205 may enter answers to questions for each disability via a corresponding abbreviated from.

Additionally or alternatively, inputs by the client 205 may be used to determine potential disabilities and ratings that may be stored in the platform environment. In some embodiments, these disabilities and ratings may be provided to a system administrator (sometimes referred to herein as a case manager) who has an understanding of the VA compensation and eCFR schedule. The system administrator may then select and/or modify the identified abbreviated forms to be provided to the user.

Each original form and each abbreviated form (sometimes referred to herein as a form group) may represent a different body joint, body, system or type of disease or disability to address hundreds of different common diagnoses or disabilities that Veterans get service-connected. The original forms may be stored in the original form database 260 in association with corresponding disabilities and/or corresponding abbreviated forms. Each abbreviated form may correspond to a unique set of conversion rules and logic for converting the abbreviated form to a corresponding completed original form. Thus, in some embodiments, each disability (or original form name) may function as a locator that may be used to reference and retrieve the abbreviated forms, conversion rules, and/or original forms. Similarly, an identifier of the original form may be used to locate conversion rules and abbreviated forms amongst the various databases. The conversion rules and logic may be specific to the disabilities, based on the Veterans Administration's laws, regulations, and medical expertise. The conversion rules and logic stored in the conversion rules database 262 may be accessed by the conversion engine 225 for mapping input data from the abbreviated form to fields included in the original form and populating the original form to generate a completed original form.

Client 205 may answer a simplified or reduced set of questions on the one or more abbreviated forms, with each abbreviated form relating to a disability of the client 205. For example, if the user 205 has three potential disabilities, the user could complete three abbreviated forms (e.g., abbreviated DBQs) via the graphical user interface 210. The abbreviated forms may be completed in electronic form such that the user could complete the forms via graphical user interface 210. Additionally or alternatively, the abbreviated forms may be forms that are received electronically and printed by the client, and scanned in via graphical user interface 210. Additionally or alternatively, another user 275 may enter answers into the abbreviated form (e.g., edit, modify or add to) or a second corresponding abbreviated form into graphical user interface 235 based on the client's feedback. As further described below, the answers or inputs the user provides are stored and used to produce a completed original form (e.g., completed original DBQ).

Conversion engine 225 may be communicatively coupled to at least one of the graphical user interfaces 210, 235 and the analysis engine 215, and may be programmed to receive the completed abbreviated forms or other relevant inputs and populate related original forms stored in original form database 260 based on corresponding conversion rules and logic stored in the conversion rules database 262. The conversion engine 225 may be configured to execute instructions to map input data extracted from fields on the abbreviated form to fields, check boxes or other areas in the original form. The conversion engine 225 may also process inputs in the abbreviated form to derive inputs for the original form. Once the original form is completed (or partially completed), quality control engine 230 may perform quality control and update the completed form for storage in completed forms database 265. Additionally or alternatively, another user 275 may log into the veteran's profile, view the completed (or partially completed) abbreviated forms and inputs therein, and perform a quality check prior to sending the completed form to a doctor for final evaluation or for submission to an approval entity.

The other user 275, who in this example may be a doctor, system administrator, underwriter, or other person with access to the platform environment 200, may modify and/or update the abbreviated and/or completed original forms via graphical user interface 235 for storage as a modified completed form. For example, a doctor may schedule an C&P evaluation with the veteran, login to the system to review the completed abbreviated form (or converted original form), and make any changes that are necessary in order to sign the completed forms. The doctor may also be able to view related documents supporting medical treatment records relevant to the user's disabilities. Once the C&P evaluation is complete, the doctor could then electronically sign the form, which could automatically apply the doctor's signature, credentials, and clinic information. The completed original form is finalized and saved in the client's profile. The system may then provide the completed original form or modified completed form to the doctor or other user for submission to the VA, for example as an email attachment. Additionally or alternatively, the system could submit the form to the VA based on the user's preference, and save a copy in a database associated with the user's profile.

Furthermore, in various implementations, the user 275 may be presented with an abbreviated form, separate from the abbreviated form provided to the client, which also corresponds to an original form. For example, multiple abbreviated forms may be associated with the original form, a first abbreviated form being completed by the client 205 and a second abbreviated form completed by the user 275. Both the first and second abbreviated forms may be used to complete the original form based on the conversion rules. For example, the doctor may be provided the second abbreviated form known as a patient evaluation survey (PES), which may be completed via graphical user interface 235. The second abbreviated form (e.g., PES) may be created in a manner substantially the same as the first abbreviated form for the client 205, except that the intent of the second abbreviated form is based on information required for input by the user (e.g., doctor). For example, similar to a first abbreviated DBQ, the PES may be a truncated version of the original DBQ to be completed by the doctor (e.g., 2-4 pages per PES versus 9-11 pages). The conversion engine 225 may receive the inputs in the second abbreviated form and apply the conversion rules to map input data extracted from the second abbreviated form to populate the original form and generate the completed original form.

Each end user (e.g., client 205 and user 275) may have their own profile that is stored in the client/user information database 252, which is assigned a status such as client, user, administrator, power administrator, or doctor. The information accessible by each user may be based on the assigned status (for data security purposes). Each end user may also be authenticated for access to the platform environment 200, for example, through input of credentials associated with the end user (e.g., a username, password, biometric, etc.)

Each user profile may comprise client/user information corresponding to each client or user from the client/user information database 252. For example, each time a doctor reviews and signs an original DBQ and/or PES, the platform environment 200 may automatically populate certain data onto each DBQ (abbreviated or original) and/or PES. Once the doctor accesses the platform environment 200, they have the ability to view profiles of clients assigned thereto, including the DBQs (abbreviated or original) to be evaluated for those clients, if any. Each DBQ (abbreviated or original) and/or PES may have a unique set of data for the doctor to evaluate and answer questions within the platform environment 200. Each DBQ (abbreviated or original) and/or PES also has data of subjective and objective symptoms to be reviewed by the doctor. Based on which DBQ (abbreviated or original) and/or PES that is to be reviewed, the platform environment 200 determines the sections the doctor is to review with the client. For example, one DBQ may require the doctor to perform range of motion testing for the knee during a C&P evaluation, while a different DBQ may require a simple interview of the client on symptoms of headaches. The platform environment 200 may determine what data must be reviewed by the doctor for each DBQ and/or PES, identify the DBQ and/or PES, and provide the document to the doctor. The platform environment 200 creates a seamless process of jumping from section-to-section to quickly go through the necessary fields to be completed by the doctor and modifies the full DBQ based on the inputs received from the doctor. Once the DBQ and/or PES is completed, the platform environment 200 provides a button for the doctor to click via a graphical user interface 235 which enters the doctor's signature (e.g., via e-signature), which places the doctor's signature on the original DBQ along with their credentials.

Once the original form is finalized, it remains in the platform environment 200 and is transferable to the client, for example, emailed as PDFs. The platform environment 200 may store all abbreviated and completed original forms which are generated and stores them with the client profile.

As described above in connection to FIG. 1, the platform environment 200 may be implemented as a web-based application with a backend server that includes a client browser application executed on a user system (e.g., user system 130), and one or more databases (e.g., application 112 and databases 114 hosted by platform server 110). Software containing conversion rules and logic for mapping input data from the abbreviated forms to fields in the original form may be stored in a database coupled to the platform environment 200. Such browser-based technology may be viewed via the browser executed on a user system. The system may extract all necessary data from the user through the abbreviated forms to auto-populate the original forms. Various embodiments provide for the completion of an original form in less than half of the time it would take to complete the original DBQ.

Platform environment 200 may advantageously be equipped with a calculator that ingests input data from the abbreviated form and determines an overall potential approval score (referred to herein as "rating"). For example, the platform environment 200 may determine a potential DR where the form is a DBQ. The VA may be configured to execute complex algorithms to determine the overall disability rating of a veteran. A calculator is useful in determining the potential overall ratings for any given client.

As an example of another application outside of the VA and DBQs, client 205 could be a person in need of renewing his or her driver's license. Client 205 could submit a driver's license number via graphical user interface 210, and analysis engine 215 could query the form query database 250 to recognize the type of form the client needs to complete. As an example, the analysis engine 215 could query form query database 250 and have the driver's license number associated with an expiration date of the user's driver's license. The analysis engine 215 may then communicate with abbreviated form engine 220 and abbreviated form database 255 storing abbreviated DMV forms to provide client 205 with an abbreviated DMV form relating to renewing a driver's license. Once client 205 completes the abbreviated DMV form, conversion engine 225 could query the original form database and conversion rules database to complete the original DMV driver's license renewal form based on one or more of the user's inputs, conversion rules, and additional information associated with the user's profile in the system. The client 205 or a DMV employee 275 may then view the completed form stored in completed forms database 265, and make any updates as needed (quality control) via graphical user interface 210 or 235 to create a modified completed form. The system could provide the completed form or modified completed form to the user for submission to the DMV, for example as an email attachment. Additionally or alternatively, the system could submit the form to the DMV for scheduling an appointment or for use during an appointment, and save a copy in a database associated with the user's profile.

FIG. 3 illustrates an example process flow performed by the platform environment for completing an original form, according to the various embodiments disclosed herein. While the illustrative process 300 depicts a single client device 305 and individual user devices 302, 304, and 306, the platform environment 200 is capable of performing the substantially same processes for multiple users and clients. That is, the process 300 may be performed for a plurality of instances, where each instance may be for multiple clients, multiple instances for a single client, or multiple sets of instances for multiple clients.

The process 300 may be performed by one or more devices in a networked environment, such as system 100 illustrated in FIG. 1, discussed above. For example, the process 300 may be executed in part by application 132 of user system 130 hosted by the backend server executing application 112 of platform server 110. In some embodiments, user system 130 may execute application 112 as a thin client to generate a graphical user interface through which the application 112 of platform server 110 may execute the process 300. In various embodiments, the process 300 may be performed partially or completely by a client 205 and/or user 275 via graphical user interfaces 210 and 235, respectively.

Process 300 will be described illustratively for completing one or more forms (e.g., DBQs). Thus, each DBQ or original form may correspond to a compensation claim (or "claim") to be submitted to the VA, and each claim may correspond to a disability. While the following description is made with reference to DBQs and compensation claims, one skilled in the art will appreciate that the scope of the embodiments herein are not so limited, and are equally applicable to other applications where any complex form may be complete.

Process 300 includes platform environment 310, which may be communicatively coupled to or otherwise include a CRM system 320. Platform environment 310 may be substantially similar to platform environment 200 of FIG. 2. Process 300 also includes a client operating client device 305 and other users each operating user devices 302, 304, 308, and 308. Each end user device may be implemented as a user system 130 of FIG. 1.

CRM system 320 may provide web-services for managing interactions between the platform environment 310 and end user devices (e.g., user devices 302, 304, 308, and 308 and client device 305). For example, the CRM system 320 may be coupled to one or more databases (e.g., one or more of database(s) 114 of FIG. 1) for storing and managing user information and status information. Example user information includes, but is not limited to, user and/or client identification information (e.g., names, social security numbers, client ID numbers, etc.), user and/or client address information, user and/or client contact information (e.g., emails addresses, phone numbers, etc.), current and potential disability ratings, and other user and/or client related information. In some embodiments, data indicative of a Quality check of the original form, which includes data extracted from one or more abbreviated forms (e.g., client self-assessment abbreviated form and/or PES completed by the doctor during the evaluation) may be included in the CRM system 320. This data follows the conversion rules created for each disability so that the VA will accept the completed original form and invalid results may disqualify the completed original form to be used in a decision. Status identifiers stored in the CRM system 320 include status updates within the platform environment 310 as described below. Any suitable CRM system may be utilized, including without limitation SugarCRM, Microsoft Dynamics CRM, Salesforce, NetSuite CRM, and the like. In some embodiments, CRM system 320 may comprise web servers remote from and communicatively coupled to the server hosting the platform environment 310. These web servers may host one or more websites and/or web-based applications for offering the web services. The CRM system 320 is communicatively coupled to and integrated with the platform environment 310. In various embodiments, the CRM system 320 is external and/or remote from the platform environment 310 and communicates with the platform environment 310. The CRM 310 may provide API that defines the manner in which the platform environment 310 may interact with the CRM system 320. In some embodiments, the CRM system 320 may be provided as a plug-in modularly programmed into the platform environment 310, for example, through the user of a software development kit (SDK).

The CRM system 320 may manage information stored in one or more of the databases and push the information to the platform environment 310 for further processing. For example, the CRM system 320 may store the client and case manager profiles and provide a gateway through which the client device 305 and user device 302 (referred to herein as "case manager" or "CM device") interact with the platform environment 310. In some embodiments, the CRM system 320 may push information to the platform environment 310 only if the client is qualified for further processing by the platform environment 310. In some embodiment, the client and user, via client device 305 and CM device 302, respectively, are not provided access to the platform environment 310. Instead, these end users interact with (e.g., receive updates, information, and provide inputs) the CRM system 320, which manages these interactions through an interface (e.g., API and/or SDK) with the platform environment 310.

Process 300 includes interactions with end users, for example, users operating user devices 302, 304, and 306 and client device 305. For example, user device 306 is illustratively depicted as a device operated by a doctor (referred to herein as "doctor device 306") that accesses the platform environment 310 via a login and authentication procedure to review, modify, and sign abbreviated and/or completed DBQs. Other illustrated users include an underwriter operating underwriter device 304 who has been authenticated for and has access to the platform environment 310 and a case manager operating CM device 302 who manages the case on the client's behalf through the CRM system 320. The client operating client device 305 may be a veteran who is seeking to submit a compensation claim to the VA. Interactions and inputs from devices 302, 304, 306, and 305 may be received via an input device included in the devices 302, 304, 306, and 305 to interact with and provide inputs into a graphical user interface, the inputs being transmitted or otherwise communicated to the platform environment 310 and/or CRM system 320.

When the client seeks to submit a claim by completing one or more original DBQs, the client signs up with the CRM system 320 using client device 305 at S1. The client inputs identification information and disability information into the CRM system 320, which creates a client profile for the client (or updates the client profile if one exists) for the CRM system 320 (referred to herein as CRM client profile) and stores the information with the CRM system 320 (e.g., in a database coupled thereto). The CRM client profile and information therein will be associated with a client ID number generated by the CRM system 320. The client may provide preliminary details of one or more disabilities for which the claim is submitted, for example, the client may identify one or more disabilities and/or symptoms (referred to as "disability information"). The client may also enter identifying information (for example, name, address, social security number), contact information (for example, address, email, phone number, etc.), information indicated veteran status (e.g., that the client is a veteran), authentication information (e.g., password, username, biometrics, etc.) and any other pertinent information.

The CRM system 320 may assign a case manager operating CM device 302 to the claim at S2. That is, the case manager may have a corresponding CM profile stored in the CRM system 320, and the CRM client profile (or information contained therein) may be associated with the CM profile. In some embodiments, the CM profile may be associated with identifying information of the assigned client, and based on the association the case manager may access some of the client information (e.g., identifying information, veteran status information, disability information). Each case manager may be assigned to one or more clients, and the assignments may be stored in a CM profile in the CRM system 320. The case manager, using CM device 302, may access at least some of the information in the CRM client profile, for example, disability information for the assigned claim and veteran status to preliminarily identify whether the client qualifies to proceed with process 300. If the case manager determines that the client qualifies, the case manager may operate CM device 302 to change a status indicator of the CRM client profile to "qualified" at S3.

In response to receiving the indication that the client is qualified to proceed, the CRM system 320 may push at least some of the information from the CRM client profile to platform environment 310. That CRM system 320 may provide the entire CRM client profile or only pieces of information necessary for completing the processes of the platform environment 310. In some embodiments, at least some of the CM profile is also pushed to the platform environment 310 along with the information from the CRM client profile and/or associated with the provided information of the CRM client profile. For example, the CRM system 320 may push at least an identifier of the case manager and contact information for association with a give claim. Using the information from the CRM system 320, a client platform profile (or account) corresponding to the client is created in the platform environment 310 at S4. The client platform profile may include a plurality of compensation claims or may correspond to a single claim. The client platform profile may include status indictors representative of the current status of each pending and/or submitted claim. At S4, the status indictor is updated to "Account Created" where there was no previous account for the client or "Claim Created" where the account exists. The client platform profile (or account) may include part or all of the information contained in the CRM client profile of the CRM system 320. For example, the client platform profile may include the disability information and identifying information. Each disability indicated in the disability information may correspond to a claim and may be associated with a separate platform status indictor representative of the current status of each respective claim.

Once the client platform profile is created or updated, the platform environment 310 automatically initiates a review of the claim(s) based on the disability information provided at S4 and the platform status to "Initial Review" at S5. Each time the platform status is updated, the platform environment 310 sends a message to the CRM system 320 to update the status within the CRM system 320, for example, at S6.

While process 300 may be performed for a plurality of claims simultaneously based on multiple disabilities identified in the disability information, the following description is made with reference to a single claim based on a single disability for illustrative purposes only.

In response to creating and/or updating the client platform profile at S4, the platform environment 310 automatically identifies an abbreviated form and retrieves it from the plurality of abbreviated forms stored in a database based on the disability information in the client platform profile at S7. The platform environment 310 packages the retrieved abbreviated form into a corresponding message and forwards the message to the client device 305 at S8. In some embodiments, the abbreviated form may be auto-populated with default values based on the disability information corresponding to the identified abbreviated form and/or may be populated with information received from the CRM system 320 (e.g., with information received at S5). In some embodiments, the message may be an email, SMS text message, MMS text message, RCS message, or the like. In some embodiments, the message includes a URL link that may direct the client device 305 to one or more webpages containing the abbreviated form to be completed as an electronic web-based form. In some embodiments, the message may also be transmitted to the CRM system 320 for access therefrom. In some embodiments, the client device 305 may have access to the platform environment 310, and the message may be provided via this access. Further still, in some embodiments, the client device 305 may receive the message or have access to the abbreviated form via an application or web-based portal on a user device. The platform status indicator pending claim is updated to "Mini Sent."

At S9, the client receives, completes, and signs the abbreviated form. The abbreviated form may be accessed by the client device 305 as an electronic form that is fillable via the client device 305 and/or as a printable form that the client prints, completes, and uploads back to the platform environment 310. Where the abbreviated form is provided via a URL link, the client may click on the link displayed by the client device 305 to access webpages containing the abbreviated form. The client electronically signs the abbreviated form and clicks on a submit button. For example, in some embodiments, a URL link is forwarded to the client device 305 that may direct the client device 305 to one or more webpages containing the abbreviated form. This submission is then sent back to the platform environment 310 at S10 and the platform status is updated to "Mini Returned" as S11.

At S12, for each returned abbreviated form, the platform environment 310 determines whether the abbreviated form has been signed by the client. For example, the platform environment 310 may determine that a signature field includes some characters based on processing the abbreviated form. If the platform environment 310 determines that there is no signature, the abbreviated form is returned to the client device 305 to complete and sign. If the platform environment 310 determines the abbreviated form has been signed, the platform status indicator for the corresponding claim is updated to "Ready for Doctor Evaluation" and the abbreviated form is forwarded to a conversion engine (e.g., conversion engine 225 of FIG. 2) at S13.

At S13, the conversion engine receives the abbreviated form and uses the abbreviated form to populate a corresponding original form. The platform environment 310 may retrieve the original form and conversion rules corresponding to the completed abbreviated form from one or more databases. The platform environment 310 then uses the conversion rules to extract input data (e.g., values input into the abbreviated form) from the abbreviated form and insert the input data to fields in the original form based on correspondences and rules in the conversion rules. At this point, the platform environment 310 may store a first version of the original form comprising input data from the client device 305.

At S13, the pending claim and corresponding abbreviated form may also be assigned to an underwriter operating an underwriter device 304. Assigning the underwriter 304 may include assigning all of the claims of a given client to the same underwriter 304 and/or assigning a plurality of underwriters to the different claims of the client. In some embodiments, the assignment of the underwriter may be done outside of the platform environment 310 by an administrator of the platform environment 310 (e.g., an administrator of the approving entity). The platform environment 310 stores an underwriter profile for each underwriter which includes identifying information, authentication information, etc. Upon assigning a claim to an underwriter, the platform environment 310 associates the claim, client, and the received abbreviated form to the underwriter profile. The underwriter profile may be associated with any number of clients and claims, which may be accessible and managed, for example, via a screen generated on a graphical user interface corresponding to the underwriter profile (for example, as illustrated in FIGS. 7A and 7B).

In some embodiments, the platform environment 310 forwards the platform status updated at S13 to the CRM system 320 to notify the case manager at S14. This notification may be passed to the client device 305. The abbreviated form may also be forwarded to the CRM system 320 at S14, and input data in the abbreviated form may be used to derive a potential rating stored in a database coupled to the CRM system 320. In various embodiments, the potential rating is determined using conversion rules for the received abbreviated form applied to the inputs on and/or input data from the abbreviated form. The determined potential rating may, for example, be used to populate a "Potential Rating" field within the client/user information database 252. In some embodiments, the completed abbreviated form received from client device 305 at S11 may be sent to the CRM system 320 prior to conversion at S13.

Figure 7D:
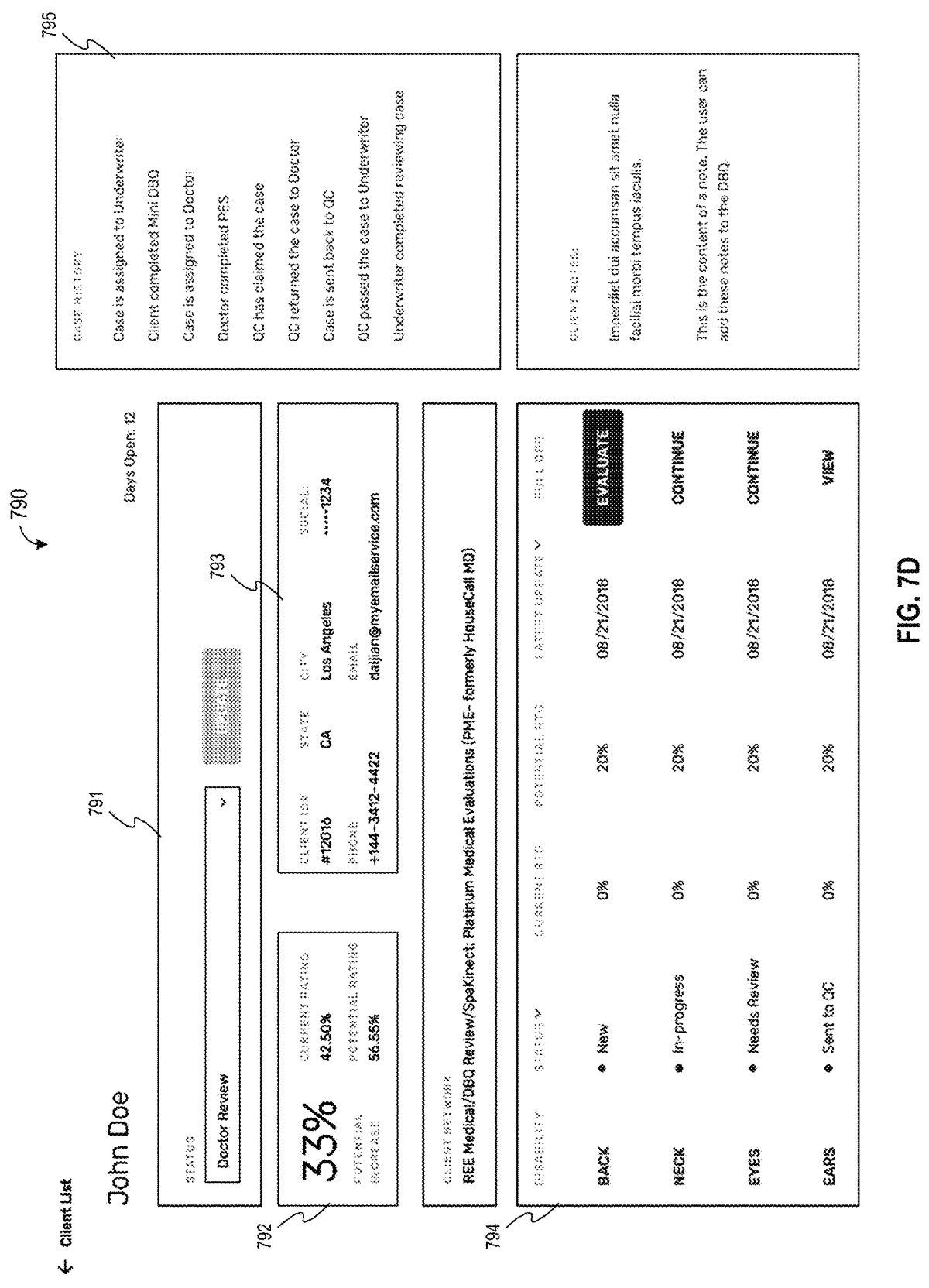

At the same time, prior to or subsequent to populating the original form, the platform environment 310 assigns a doctor operating a doctor device 306 to the pending claim corresponding to the abbreviated DBQ at S15. Assigning the doctor may include assigning all of the client's claims to the same doctor and/or assigning the doctor to one or more of the pending claims and assigning a different doctor to others. In some embodiments, assignment of the doctor may be done outside of the platform environment 310 by an administrator of the platform environment 310 (e.g., an administrator of the approving entity) or may be automated by the platform environment 310. Each doctor having access to the platform environment 310 via doctor device 306 may have a doctor profile stored within the platform environment 310 which includes identifying information, signature information, credentials (e.g., license number), phone number, title information, authentication information, etc. Upon assigning a claim to a doctor, the platform environment 310 associates the claim and client with the doctor profile. The doctor profile may be associated with any number of clients and claims, which may be accessible and managed, for example, via screens generated on a graphical user interface corresponding to the underwriter profile (for example, as illustrated in FIGS. 7C and 7D).

In various embodiments, assigning a doctor at S15 may be based, in part, on the potential rating determined at S13. For example, a doctor may be assigned if the potential rating from the abbreviate form is above a threshold and/or is indicative that the current potential rating (e.g., as determined by the platform environment 310) and/or actual rating (e.g., as provided by the VA) for the client is eligible for an increase. In some embodiments, the current potential rating and/or actual rating may be a rating corresponding to a single disability (e.g., the disability for which the abbreviated form was completed). In this case, at S13, the platform environment 310 determines a potential rating from the abbreviated form, and, if the determined potential rating is greater than an existing rating (or is a first rating) for that disability, a doctor may be assigned to evaluate the client. If the results from the abbreviated form do not show an increase, then that disability will not be evaluated by the doctor. In another embodiment, the current potential rating and/or actual rating may be a rating representative of all claims submitted by the client (e.g., a single rating for all disabilities). In this case, at S13, the platform environment 310 determines a potential rating for the abbreviated form, adds this determined potential rating to the current potential and/or actual rating to determine an overall potential rating, and, if the determined overall potential rating is greater than the current potential and/or actual rating (or is a first rating), a doctor may be assigned to evaluate the client. If the results from the abbreviated form do not show an increase, then that disability will not be evaluated by the doctor.

Once a doctor is assigned to a pending claim, the doctor may schedule an evaluation with the client and the platform status indicator may be updated to "Evaluation Scheduled." In some embodiments, following S13, the case manager and/or underwriter may, via a respective user device, review the abbreviated form and the potential rating, contact the client, and verify the client would like to proceed with the claim. The evaluation with the doctor may then be scheduled.

At S16, in some embodiments, the doctor device 306 may receive an abbreviated form corresponding to the assigned pending claim. As described herein, the abbreviated form is based on the disability underlying the assigned claim. In one embodiment, the received abbreviated form may be the abbreviated form completed by the client, for example, where the abbreviated form includes fields for inputs by both the client and the doctor. In another embodiment, the received abbreviated form may be a second abbreviated form (e.g., a PES) that corresponds to the original form and disability underlying the pending claim. The received abbreviated form may be associated with the doctor profile, which may be updated with access to the received abbreviated form via a link. The screens graphically displayed via the graphical user interface of the doctor device 306 may display the link through which the doctor device 306 may access the received abbreviated form. The platform status may be updated to "Doctor Reviewing DBQ." At S17, the doctor may evaluate the client and complete and sign the abbreviated form by entering inputs into the fields of the abbreviated form. Where the received abbreviated form is the abbreviated form completed by the client, the doctor device 306 may edit the inputs provided by the client device 305 following the evaluation.

At S18, the completed abbreviated form is provided to the conversion engine and the original form is populated based on the inputs in the abbreviated form from doctor device 306. That is, input data (e.g., field values) are extracted from the abbreviated form received from the doctor device 306 and used to populate fields in the original form based on conversion rules corresponding to the abbreviated form. The platform status is then updated to "Final Review" and access to the original form is provided to the underwriter device 304. The underwriter device 304 may receive status updates of the completed abbreviated form at S18 and the conversion to the original form thereafter. In some embodiments, the underwriter, via underwriter device 304, performs a foundation check and then assigns the original form to quality control device 308 at S19. The original form is forwarded to a quality control engine (e.g., quality control engine 230 of FIG. 2) for access by the assigned quality control device 308 at S20, for example, via a graphical user interface displaying user interaction screens. The platform status is also updated at S20 to "DBQ Quality Control."

Then quality control device 308 reviews the original form and signs the original form at S21. The original form is reviewed to confirm that it is fully and accurately completed, for example, that every field of the original form comprises at least one input data and that the input data matches that from the abbreviated form. The abbreviated form is also reviewed to confirm that inputs in each field are at least related to the queries corresponding to each field. In various embodiments, the conversion rules may function as a form of quality control (e.g., automated quality control executed by the platform environment 310 without user evaluation), because the conversion rules prevent contradictory inputs entered into an abbreviated form from being translated into the original form. If the conversion rules detect that a data input from the abbreviated form from the client device 305 (and/or the abbreviated form from the doctor device 306) do not conform with the conversion rules, the original form will not pass quality control. Additionally, the conversion rules for each disability ensure that invalid data inputs are not used for values for the original form, for example, the conversion rules ensures invalid results for a Range of Motion evaluation entered into an abbreviated DBQ or a PES are not translated into the completed original DBQ.

At S22, the process 300 determines whether the original form passes quality control or not. If no, comments as to why the original form was not approved are included with the original form as additional metadata and the platform status is updated to "QC Returned?". In some embodiments, the original form and comment metadata are then sent to the underwriter device 304 and/or to the doctor device 306 at S23. The status may be updated in the CRM system 320 at S24. The platform environment 310 may then repeat S6 through S10 to correct the abbreviated form and/or the abbreviated form may be sent to the case manager device 302 to be addressed with the client. Similarly, the platform environment 310 may repeat S15-S18 to have the doctor correct the abbreviated form. Once the abbreviated form is corrected, the original form may be updated using the conversion rules and S19-S24 may be repeated on the corrected original form.

If, at S22, platform environment 310 determines the abbreviated form passes quality control, the platform status is updated to "Final Review" and uploaded for final review by underwriter device 304 at S25. Once approved, at S25, the original form may be sent to the CRM system 320 at S26 and the case manager may provide the original form to the client device 305 at S27. The platform status may be updated at S28 and/or S27 to "Underwriting Process Complete." The client device 305 may receive the completed original form at S29, review the completed original form and send the original form to the approving entity 307 (e.g., the VA) at S30.

While the example provided above describes the quality control engine as reviewing the completed original form, other configurations are possible. For example, each completed abbreviated form (e.g., from client device 305 and/or doctor device 306) may be subject to quality control review via steps S18-S23 to ensure accuracy throughout the process 300.

FIGS. 4A through 4D illustrate an example abbreviated form, according to the various embodiments disclosed herein. For example, each of FIGS. 4A through 4D illustrate a portion of an abbreviated form. In the illustrative example, abbreviated form 400 is an abbreviated DBQ corresponding to a disability, for example, post-traumatic stress disorder (PTSD). The abbreviated form 400 comprises a plurality of fields M1 through M58 that correspond to questions or queries 401-458 related to the disability corresponding to the abbreviated form. Abbreviated form 400 also illustratively includes an abbreviated form identifier 460 (e.g., "VBA-MDBQ-2019-01"). As described above, the abbreviated form is created based on the original intent of a corresponding original form, such that all necessary information for completing the original form may be provided via the abbreviated form.

The abbreviated form 400 may be provided to the client in accordance with the various embodiments described herein. For example, the abbreviated form 400 may be stored in one or more databases, such as, for example, the abbreviated form database 255 of FIG. 2. The abbreviated form 400 may be retrieved by the platform environment (e.g., platform environment 200 and/or platform environment 310) based on inputs received from the client and/or case manager describing a disability and/or symptoms. The analysis engine may identify the disability in the form query database and identify the abbreviated form for retrieval from the abbreviated form database by the abbreviated form engine. The abbreviated form 400 may be packaged as described above and provided to the client.

The abbreviated form 400 may be accessed via a web-based portal, application, etc., as described herein and completed by the client. In some embodiments, each portion of abbreviated form 400 shown on FIGS. 4A-4D, respectively, may be a page of an abbreviated form, for example, where the abbreviated form 400 is a printable electronic document (e.g., a PDF or similar). In another embodiment, an end user may scroll through a single document containing all portions of the abbreviated form 400. For example, the client may interact with a graphical user interface displaying the abbreviated form 400 and, using an input device, input information into each field. The information entered into each field may be extracted by the platform environment (e.g., platform environment 200 and/or platform environment 310) as input data that is stored in the abbreviated form database and associated with the abbreviated form (e.g., using an abbreviated form locator). The data inputs for each field may be stored in association with the field and query, for example, input data for field M1 may be stored in association with the field M1 and query 401. Thus, the completed abbreviated form 400 is processed and the input data extracted for subsequent processing.

FIGS. 5A through 5E illustrate another example abbreviated form, according to the various embodiments disclosed herein. The abbreviated form 500 depicted in FIGS. 5A through 5D is similar to the abbreviated form 400, except that the abbreviated form 500 includes different queries 501-573. That is, the abbreviated form 500, in the illustrative example, is a second abbreviated DBQ corresponding to the same disability as the abbreviated form 400, except that the abbreviated form 500 is to be completed by another end user. In this case, the abbreviated form 500 is a PES corresponding to the abbreviated form 400 that is to be completed by the doctor. The abbreviated form 500 comprises a plurality of fields P1 through P73 which correspond to the queries 501-573. The abbreviated form 500 also illustratively includes an abbreviated form identifier 574 (e.g., "VBA-PES-2019-01"). As described above, the second abbreviated form may be created based on the original intent of a corresponding original form, such that all necessary information for completing the original from may be provided via the second abbreviated form 500.

The abbreviated form 500 may be provided to the end user (e.g., doctor device 306 of FIG. 3) in accordance with the various embodiments described herein. For example, the abbreviated form 500 may be stored in one or more databases, such as, for example, the abbreviated form database 255 of FIG. 2. The abbreviated form 500 may be retrieved by the platform environment (e.g., platform environment 200 and/or platform environment 310) in response to the platform environment 310 receiving a completed abbreviated form 400 from the client. The analysis engine may identify the second abbreviated form for retrieval from the abbreviated form database by the abbreviated form engine as described above. The abbreviated form 500 may be associated with the end user in the platform environment 310 via the end user profile and provided as a link displayed by the graphical user interface.

The abbreviated form 500 may be accessed via a web-based portal, application, etc., as described herein and completed by the end user. For example, the end user may interact with a graphical user interface displaying the abbreviated form 500, and, using an input device, input information into each field. The information entered into each field may be input data that is stored in the abbreviated form database. The input data for each field may be stored in association with the field and query, for example, data inputs for field P1 may be stored in association with the field P1 and query 501. Thus, the completed abbreviated form 500 may then be processed and the data inputs extracted for subsequent processing.

FIGS. 6A through 6F illustrate an example original form, according to the various embodiments disclosed herein. The original form 600 depicted in FIGS. 6A through 6F is similar to the abbreviated form 400, except that the original form 600 includes the full original form to which the abbreviated form 400 and/or the abbreviated form 500 correspond. That is, the original form 600, in the illustrative example, is the original DBQ for the disability corresponding to the abbreviated form 400 and/or the abbreviated form 500. The original form 600 comprises a plurality of fields D1 through D163 which correspond to the queries 601-763. The original form 500 also illustratively includes a form identifier 764 (e.g., "VA FORM 21-0960P-3" or "21-0960P-3").

The original form 600 may be stored in one or more databases, such as, for example, the original form database 260 of FIG. 2. The original form 600 may be retrieved by the platform environment (e.g., platform environment 200 and/or platform environment 310) in response to the platform environment 310 receiving the completed abbreviated form 400 and/or the abbreviated form 500. The completion engine may identify the original form for retrieval from the original database by the conversion engine as described above.

The original form may be populated based on one or more of the abbreviated form 400 and the abbreviated form 500. For example, the conversion engine may retrieve conversion rules defining a mapping of at least some of the input data corresponding to fields M1-M58 in the abbreviated form 400 to one or more fields D1-D163 of the original form. Similarly, at least some of the input data from fields P1-P73 in the abbreviated form 500 may be mapped to one or more fields D1-D163 of the original form using the conversion rules. The mapping may be used by the platform environment 310 to populate each field D1-D163 with a value based on the correspondences between the various fields and inputs defined by the conversion rules. In some embodiments, the values for fields D1-D163 may be the same as the input data for the corresponding fields M1-M58 and/or P1-P73. Additionally, in some embodiments, some values for populating one or more fields D1-D163 may be derived based on inputs in the abbreviated form and an algorithm.

What follows is an example of conversion rules for converting the abbreviated form 400 and the abbreviated form 500 to the original form 600. The conversion rules may be stored as a set of instructions within the conversion rule database, that when executed by the platform environment 200 and/or 310 (e.g., by a processor therein) are configured to map the input data from the abbreviated forms 400 and 500 to the original form 600.

For example, with reference to FIGS. 3-6F, once the abbreviated forms are completed, the underwriter reviews each abbreviated form for completion and accuracy. Based on the results from the abbreviated form, the platform environment 310 will convert the input data into a rating and populate the "Potential Rating" field in the CRM client profile and/or the platform client profile. After reviewing the results for each abbreviated form, the underwriter may decide which disabilities to have evaluated by a doctor by checking a box "To Be Evaluated" in a graphical user interface executed by the platform environment 310. This status update may also sync with the CRM system 320 to display the same information to the case manager for review and informing the client.

In various embodiments, a set of default values may correspond to a first set of fields in the original form 600. That is, upon retrieving the original form 600, default values may be retrieved from a conversion rule database based on queries in the original form 600 corresponding to the fields. Table 1 provides illustrative defaults for the original form 600 related to PTSD.

TABLE 1

D7 = Selected
D10 = "F43.1"
D11 = Selected
D39 = Selected
D42 = Selected
D46 = Selected
D51 = Selected
D63 = Selected
D71 = Selected
D74 = "VA disabilities list reviewed, no tx records available"
D80 = "None"
D85 = Selected
D86 = Selected
D108 = Selected
D111 = Selected
D154 = Selected
D157 = "Session was a one-time evaluation with the Veteran. Veteran was made aware of the nature of this TABLE 1-continued one-time session. No treatment
recommendation was made at the
end of the session. The purpose of
this session was to assess the
presence and severity of the
Veteran's service-related disability."

In various embodiments, information stored in the CRM system 320 may be used to populate the original form 600. For example, the original DBQ form "PTSD" entered into the CRM system may retrieve the original form 600. Then client identification information in the CRM system 320 may be used to populate fields in the original form 600. For example, the client's first name may be used to populate field D1 and the client's last name may be used to populate field D3. Similarly, the first three numbers of the client's social security number may be used to populate fields D4, D32, D66, D82, D114, and D151; the middle two numbers may populate D5, D33, D67, D83, D115, and D152; and the last four numbers may populate D6, D34, D68, D84, D116, and D153. The disability name may be used to populate D9.

Once the abbreviated form 400 is completed by the client, some of the information contained within it may be used to determine the rating for this disability. This rating may be used to populate the "Potential Rating" field within the CRM system 320. For example, mental disabilities (PTSD/Non-PTSD) can only produce the following ratings: 10, 30, 50, 70, or 100, based on the regulations. Each rating is broken up into a group of symptoms. The following symptoms selected in identified fields would fall under the following respective rating:

100
M6, M7, M8, M9, M10, M11, and M12
70
M14, M15, M16, M17, M18, M19, M20, M21, and M22
50
M24, M25, M26, M27, M28, M29, M30, M31, and M32
30
M34, M35, M36, M37, M38, and M39

In the illustrative example, the highest rating should always prevail according to the following rules. If 2 or more items are selected under the 100 category, the Potential Rating is set to "100". If fewer than 2 items are selected, then "100" cannot be the potential rating. If 3 or more items are selected under the "70" category, the Potential Rating is set to "70". If fewer than 3 items are selected, then "70" cannot be the potential. If 3 or more items are selected in the "50" category, the Potential Rating is set to "50". If 3 or more items are selected under the "30" category, the Potential Rating is set to "30". For example, if a client selects 4 in each category except 100, where they select 1, then the potential rating should be 70, since 70 is the highest rating possible according to these example conversion rules.

The conversion rules may also include direct mapping of inputs in the abbreviated form 400 to fields in the original form 600. For example, Table 2 illustrates at least some of the correspondence between the abbreviated form 400 and the original form 600.

TABLE 2

M1 [textbox] = D75 [textbox]
M2 [textbox] = D76 [textbox]
M3 [textbox] = D77 [textbox]
M4 [textbox] = D78 [textbox]
M5 [textbox] = D79 [textbox]

TABLE 2-continued

M6 = D133
M7 = D142
M8 = D143
M9 = D144
M10 = D146
M11 = D147
M12 = D126
M14 = D138
M15 = D139
M16 = D129
M17 = D122
M18 = D136
M19 = D140
M20 = D141
M21 = D145
M22 = D137
M24 = D127
M25 = D128
M26 = D121
M27 = D130
M28 = D125
M29 = D131
M30 = D132
M31 = D134
M32 = D135
M34 = D118
M35 = D123
M36 = D124
M37 = D117
M38 = D119
M41 = D56
M39 = D120
M42 = D57
M43 = D58
M44 = D59
M45 = D60

In some embodiments, not all of the inputs in the abbreviated form 400 will be used to populate the original form 600. For example, fields M13, M23, M33, and M40 are included in the abbreviated form 400 but do not transfer to the original form 600. In some embodiments, this information may be for internal use and helps the client describe the symptoms to enable greater clarification on the part of the underwriter and/or doctor.

Once the client completes the abbreviated form 400 and all necessary information is extracted and transferred to the original form 600, this becomes the first version of the original DBQ stored in the completed forms database. The underwriter may review this version and make any necessary changes. The original DBQ may also be editable within the platform environment by the underwriter and any changes made will be carried over into subsequent versions of the original form (e.g., a second version upon being edited by the underwriter).

In various embodiments, information stored in the CRM system 320 may be used to populate the second abbreviated form 500 (e.g., the PES). For example, client identification information in the CRM system 320 may be used to populate fields in the second abbreviated form 500. The client's first and last name may be used to populate fields P1, P7, P20, P43, and P66 and the last four numbers of the client's social security number may be used to populate fields DP2, P8, P21, P44, and P67. Similarly, the first version of the original DBQ (or second version where the underwriter has entered edits) may be used to populate fields in the second abbreviated form 500 for review, for example, where the queries in the second abbreviated form 500 are addressed by the client in the first abbreviated form 400.

Once the second abbreviated form 500 is completed by the doctor, some of the information contained within it may be used to determine the rating for this disability. The information may alter and/or maintain the potential rating previously established by the first abbreviated form 400. Similarly, the rating may be used to populate or update the "Potential Rating" field within the CRM system 320. For example, as with the first abbreviated form 400, mental disabilities (PTSD/Non-PTSD) can only produce the following ratings: 10, 30, 50, 70, or 100. Each rating is broken up into a group of symptoms. The following symptoms selected in identified fields would fall under the following respective rating:

100

P30, P31, P32, P33, P34, P35, and P36

70

P37, P38, P39, P40, P41, P42, P45, P46, and P47

50

P48, P49, P50, P51, P52, P53, P54, P55, and P56

30

P57, P58, P59, P60, P61, and P62

In the illustrative example, the highest rating should always prevail according to the following rules. If 2 or more items are selected under the 100 category, the Potential Rating is set to "100". If fewer than 2 items are selected then "100" cannot be the potential rating. If 3 or more items are selected under the "70" category, the Potential Rating is set to "70". If fewer than 3 items are selected, then "70" cannot be the potential. If 3 or more items are selected in the "50" category, the Potential Rating is set to "50". If 3 or more items are selected under the "30" category, the Potential Rating is set to "30". For example, if a doctor selects 4 in each category except 100, where they select 1, then the potential rating should be 70, since 70 is the highest rating possible according to the example conversion rules.

The conversion rules may also include direct mapping of inputs in the second abbreviated form 500 to fields in the original form 600. For example, Table 3 illustrates at least some of the correspondence between the second abbreviated form 500 and the original form 600.

TABLE 3

P4 = D75
P5 = D76
P6 = D77
P9 = D78
P10 = D79
P11 = D88
P12 = D89
P13 = D90
P14 = D91
P15 = D92
P16 = D94
P17 = D95
P18 = D96
P19 = D97
P22 = D98
P23 = D99
P24 = D100
P25 = D102
P26 = D103
P27 = D104
P28 = D105
P29 = D106
P30 = D133
P31 = D142
P32 = D143
P33 = D144
P34 = D146
P35 = D147
P36 = D126
P37 = D138
P38 = D139

TABLE 3-continued

P39 = D129
P40 = D122
P41 = D140
P42 = D141
P45 = D145
P46 = D136
P47 = D137
P48 = D127
P49 = D128
P50 = D121
P51 = D130
P52 = D125
P53 = D131
P54 = D132
P55 = D134
P56 = D135
P57 = D118
P58 = D123
P59 = D117
P60 = D124
P61 = D119
P62 = D120
P63 = D56
P64 = D57
P65 = D58
P68 = D59
P69 = D60
P70 = D148
P71 = D149
P72 = D15

In some embodiments, not all of the inputs in the second abbreviated form 500 will be used to populate the original form 600. For example, fields P3 and P73 are included in the second abbreviated form 500 but do not transfer to the original form 600. In some embodiments, this information may be for internal use.

The doctor may review the PES and make any necessary changes to the second abbreviated form 500. The second abbreviated form 500 may then be uploaded or saved to the platform environment 310 and used to create the final version of the original form 600, for example, by auto-populating the fields based on the above correspondences. After the second abbreviated form 500 is complete and the original form 600 populated, the original form 600 may be signed on the spot by the doctor. This finalized version of the original form 600 will uploaded back into the platform environment 310 for a final check by the quality control engine as described above.

While the foregoing example is described with reference to DBQs related to PTSD as an example disability, it will be appreciated that the process applies similarly for any other disability, for example, but not limited to, mental disorders other than PTSD, sinusitis, headaches, shoulder injuries, etc. Each disability will correspond to a uniquely created first abbreviated form, a uniquely created second abbreviated form, and an original form. The original form may be populated based on a mapping derived from uniquely structured conversion rules based on the disability. Thus, the foregoing is merely an illustrative example.

The processes disclosed herein provide numerous non-limiting advantages over the conventional electronic form submission and for auto-population for electronic forms using human interactions. For example, the VA rejects most private DBQs because physicians do not complete them properly and fail to adhere to the strict VA guidelines. The transfer of data inputs from the abbreviated forms (e.g., abbreviated DBQs and PESs) onto the original form uses the conversion rules that are based on the knowledge, training, and experience resulting from processing the forms for the VA and the USC 38 CFR Parts 3 & 4. The abbreviated forms and conversion rules require a deep understanding of what the VA (or any approving entity) will accept. That is, each original DBQ being used requires its own set of unique rules, as every original DBQ deals with a different body part or body system. No two original DBQs are exactly alike. Thus systems herein will store and manage numerous abbreviated forms and conversion rules for numerous different original DBQs. The conversion rules for each are based on comprehensive training and understanding of USC 38 CFR Parts 3 & 4, which govern how to properly adjudicate VA disability claims.

Advantageously, the systems described herein may generate several original forms in the time it takes to manually complete just one form. For example, systems herein may generate 5, 6, or more original DBQs before a single original DBQ can be completed manually. This may be a result of the processes and functions described herein, which are not currently being employed by the VA or conventional form completion system. Original DBQs may include subjective and objective sections to be completed, and the systems disclosed herein may be configured to obtain the subjective info from the client and the objective info from the physician and combine this information included in abbreviated DBQs to complete the original DBQ. Thus, the systems herein streamline the DBQ-completion process to efficiently use the doctor's time and knowledge.

Furthermore, the doctor and/or other users are not required to have special training. The graphical user interface provides simple, concise and efficient access to information and links to necessary forms to be completed. Any doctor or user would be able to step in, evaluate a client, and properly complete a DBQ that the VA (or other approving entity) will accept. Conventional systems for submission of complex medical-related forms do not provide this ease of access. In fact, the VA currently offers cumbersome training to physicians for completing DBQs via C&P exams, which is ineffective as compared to the systems disclosed herein.

Furthermore, the above process is not limited to only disabilities and/or compensation claims, for example, the DMV use case provided above illustrates another example. The processes herein may be applied to any standardized, complex form that can be truncated into one or more abbreviated forms based on the intended purpose of the original form and a set of conversion rules that may be generated for auto-populating the original form using inputs in the abbreviated form.

FIGS. 7A through 7D illustrate example screens generated by the system of FIG. 2 and displayed on an end user device, according to the various embodiments disclosed herein. The graphical user interface may be executed to display screens 770, 775, 781, and 790 on a display of a user system including, but not limited to, a computer monitor, TV, touchscreen display of a mobile device, a laptop display screen, or any other display device that may be apparent to a person of ordinary skill in the art. For example, the graphical user interface may be executed by one or more devices in a networked environment such as the example system 100 illustrated in FIG. 1 and/or example platform environment 200 illustrated in FIG. 2 discussed above. In some embodiments, graphical user interfaces may be executed by a client (e.g., thin or thick client as described in connection to FIG. 1) installed on a user system 130 for displaying a plurality of screens. Screens 770, 775, 781, and 790 are example screens displayed by the graphical user interface, and the graphical user interfaces described herein may be configured to display various other screens in accordance with the embodiments disclosed herein.

FIG. 7A illustrates example a client list screen 770 executed on an end user device operated by an underwriter (e.g., underwriter device 304 of FIG. 3). From screen 770, the underwriter may review, manage, and access information included in the platform environment for all assigned clients. The information displayed therein may be retrieved from the various databases described throughout the present disclosure and used to populate the portions of screen 770 as illustrated in FIG. 7A. A first portion 771 lists all items that need review, for example, by identifying a client by name and case number. The underwriter may click on an item to access information for review (e.g., abbreviated forms and/or original forms). A second portion 772 includes a list of all clients assigned to the underwriter. The client list identifies the client name, case number, location information, disability information, and number of original forms (e.g., DBQs) that are pending and/or submitted. The client list portion 772 also includes a case status identifier that may be updated based on the platform status as described above.

Selecting a client from a portion 772 of a screen 770 causes the graphical user interface to generate and display a client information screen 775. The client information screen 775 provides information and access to other information within the platform environment for a given client. The information displayed therein may be retrieved from the various databases described throughout the present disclosure and used to populate the portions of screen 775 as illustrated in FIG. 7B. A first portion 776 provides the platform status and assigned underwriter. A second portion 777 graphically displays a current rating based on DBQs that have been submitted to the VA and a potential rating. This potential rating may be a derived potential rating based on the current rating and pending original form submissions. The potential increase represents a difference between the current rating and the potential rating. A third portion 778 displays client identifying information, for example, client ID number, state and city, social security number, phone number, and email. A fourth portion 779 provides a list of disabilities, a check box selectable by the underwriter as to whether the client needs to be evaluated by a doctor for each disability or that the claim is ready for evaluation, current ratings for each disability, potential ratings for each disability as described above, a link to access an abbreviated form corresponding to each disability, a link to access a second abbreviated form (e.g., PES) corresponding to each disability, a link to an original form (completed or not), and date of last update. In some embodiments, where one or more of the forms needs to be reviewed by the underwriter, a review link maybe included in association with the disability and necessary forms. Whereas, if the form(s) have been reviewed and submitted, the underwriter may only be able to view the forms, in which case the review link is replaced with a view link. Additionally, a fifth portion 780 provides a case history and comments from clients.

FIGS. 7C and 7D are similar to FIGS. 7A and 7B in that they illustrate a client list screen 781 and a client information screen 790, respectively. Similarly, the information displayed therein may be retrieved from the various databases described throughout the present disclosure and used to populate the portions of screens 781 and 790 as illustrated. However, unlike the screens 770 and 775, the screens 781 and 790 are displayed on a user system operated by a doctor.

From a screen 781, the doctor may review, manage, and access information included in the platform environment for all assigned clients. A first portion 782 lists all items that need review, for example, by identifying a client by name and client ID number. The doctor may access information for a given client by clicking on the appropriate region of a first portion 782. A second portion 783 includes a list of all clients assigned to the doctor. The client list identifies the client name, client ID number, location information, disability information, and number of original forms (e.g., DBQs) that are pending and/or submitted. The client list portion 783 also includes a case status identifier that may be updated based on the platform status as described above.

Selecting a client from second portion 783 of screen 781 causes the graphical user interface to generate and display a client information screen 790. The client information screen 790 provides information and access to other information within the platform environment for a given client. A first portion 791 provides the platform status. A second portion 792 graphically displays a current rating based on DBQs that have been submitted to the VA and a potential rating, as described above. A third portion 793 displays client identifying information, for example, client ID number, state and city, social security number, phone number, and email. A fourth portion 794 provides a list of disabilities, an indicator of the status for each disability (e.g., new, in-progress, needs review, sent to QC), current ratings for each disability, potential ratings for each disability as described above, a date of last updated, and a link to access a second abbreviated form corresponding to each disability. The link may be displayed as "Evaluate" where the doctor has yet to being review of the linked document, "Continue" where the doctor has started but not completed review of the linked document; and "View" where the doctor has completed the review and submitted the second abbreviated form to the platform environment for QC. Additionally, a fifth portion 795 provides a case history and comments from clients.

Figure 8:
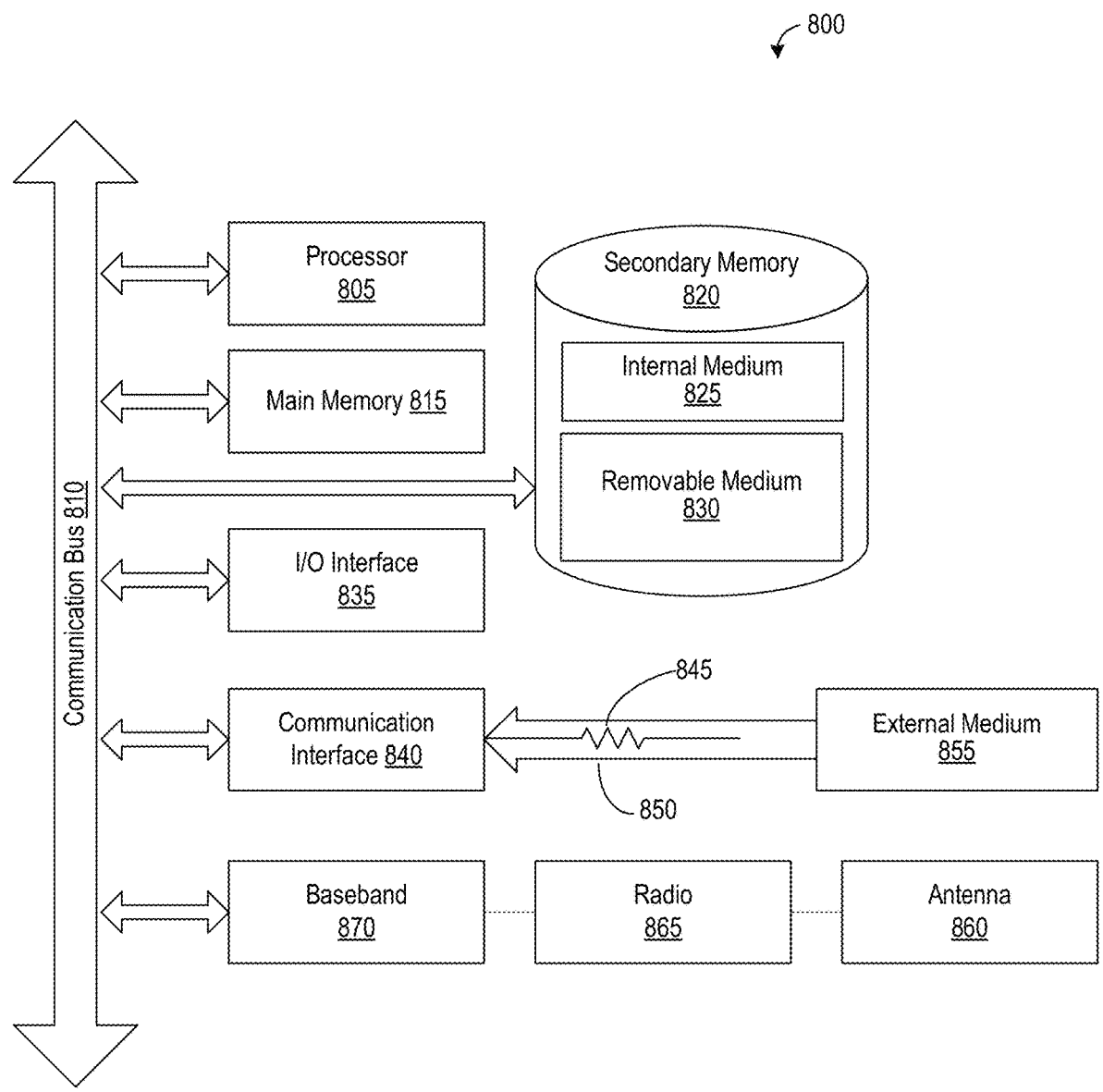
FIG. 8 illustrates an example wired and/or wireless computer device suitable for use in the systems disclosed herein.

FIG. 8 illustrates an example wired and/or wireless computer device suitable for use in the systems disclosed herein. Referring to FIG. 1, the system 800 may be used to implement the user system 130, the platform server 110, and/or the CRM system 140. The system 800 may be programmed with software comprising instructions that, when executed by at least one processor, cause the system 130 to perform the various functions, processes, and/or methods described herein, for example, as described in connection to FIGS. 2 and/or 3.

In various embodiments, the system 800 can be a conventional personal computer, computer server, personal digital assistant, smart phone, tablet computer, or any other processor-enabled device that is capable of wired or wireless data communication. Other computer systems and/or architectures may be also used, as will be clear to those skilled in the art.

The system 800 preferably includes one or more processors, such as processor 805. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 805.

The processor 805 is preferably connected to a communication bus 810. The communication bus 810 may include a data channel for facilitating information transfer between storage and other peripheral components of the system 800. The communication bus 810 further may provide a set of signals used for communication with the processor 805, including a data bus, address bus, and control bus (not shown). The communication bus 810 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 800 preferably includes a main memory 815 and may also include a secondary memory 820. The main memory 815 provides storage of instructions and data for programs executing on the processor 805. For example, the main memory 815 may provide storage for the analysis engine 215, the abbreviated form engine 220, the conversion engine 225, the QC engine 230, and the graphical user interface 235, which may be representative of software modules that, when executed by the processor 805, perform the functions described in FIGS. 2 and 3. As another example, the main memory 815 may be illustrative of one or more of databases 250, 252, 255, 260, 262, and/or 265 and thus provide storage of the data and information stored therein. The main memory 815 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 820 may optionally include an internal memory 825 and/or a removable storage medium 830, for example a floppy disk drive, a magnetic tape drive, a compact disc ("CD") drive, a digital versatile disc ("DVD") drive, etc. The removable storage medium 830 is read from and/or written to in a well-known manner. Removable storage medium 830 may be, for example, a floppy disk, magnetic tape, CD, DVD, SD card, etc.

The removable storage medium 830 is a non-transitory computer readable medium having stored thereon computer executable code (i.e., software) and/or data. The computer software or data stored on the removable storage medium 830 is read into the system 800 for execution by the processor 805.

In alternative embodiments, the secondary memory 820 may include other similar means for allowing computer programs or other data or instructions to be loaded into the system 800. Such means may include, for example, an external storage medium 855 and a communication interface 840. Examples of external storage medium 855 may include an external hard disk drive or an external optical drive, or and external magneto-optical drive.

Other examples of secondary memory 820 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are the removable storage medium 830 and a communication interface, which allow software and data to be transferred from an external storage medium 855 to the system 800.

System 800 may also include an input/output ("I/O") interface 835. The I/O interface 835 facilitates input from and output to external devices. For example the I/O interface 835 may receive input from a keyboard, mouse, touch screen, gestures detecting camera, speech command module, etc. and may provide output to a display generated by the graphical user interface. The I/O interface 835 is capable of facilitating input from and output to various alternative types of human interface and machine interface devices alike.

System 800 may also include a communication interface 840. The communication interface 840 allows software and data to be transferred between system 800 and external devices (e.g. printers), networks, or information sources. For example, computer software or executable code may be transferred to system 800 from a network server via communication interface 840. Examples of communication interface 840 include a modem, a network interface card ("NIC"), a wireless data card, a communications port, a PCMCIA slot and card, an infrared interface, and an IEEE 1394 fire-wire, just to name a few.

Communication interface 840 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via the communication interface 840 are generally in the form of the electrical communication signals 845. The electrical communication signals 845 are preferably provided to the communication interface 840 via a communication channel 850. In one embodiment, the communication channel 850 may be a wired or wireless network, or any variety of other communication links. The communication channel 850 carries the electrical communication signals 845 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 815 and/or the secondary memory 820. Computer programs can also be received via the communication interface 840 and stored in the main memory 815 and/or the secondary memory 820. Such computer programs, when executed, enable the system 800 to perform the various functions of the present invention as previously described.

In this description, the term "computer readable medium" is used to refer to any non-transitory computer readable storage media used to provide computer executable code (e.g., software and computer programs) to the system 800. Examples of these media include the main memory 815, the secondary memory 820 (including the internal memory 825, the removable storage medium 830, and the external storage medium 855), and any peripheral device communicatively coupled with the communication interface 840 (including a network information server or other network device). These non-transitory computer readable mediums are means for providing executable code, programming instructions, and software to the system 800.

In an embodiment that is implemented using software, the software may be stored on a computer readable medium and loaded into the system 800 by way of removable storage medium 830, I/O interface 835, or communication interface 840. In such an embodiment, the software is loaded into the system 800 in the form of electrical communication signals 845. The software, when executed by the processor 805, preferably causes the processor 805 to perform the inventive features and functions previously described herein.

The system 800 also includes optional wireless communication components that facilitate wireless communication over a voice and over a data network. The wireless communication components comprise an antenna system 860, a radio system 865 and a baseband system 870. In the system 800, radio frequency ("RF") signals are transmitted and received over the air by the antenna system 860 under the management of the radio system 865.

In one embodiment, the antenna system 860 may comprise one or more antennae and one or more multiplexors (not shown) that perform a switching function to provide the antenna system 860 with transmit and receive signal paths. In the receive path, received RF signals can be coupled from a multiplexor to a low noise amplifier (not shown) that amplifies the received RF signal and sends the amplified signal to the radio system 865.

In alternative embodiments, the radio system 865 may comprise one or more radios that are configured to communicate over various frequencies. In one embodiment, the radio system 865 may combine a demodulator (not shown) and modulator (not shown) in one integrated circuit ("IC"). The demodulator and modulator can also be separate components. In the incoming path, the demodulator strips away the RF carrier signal leaving a baseband received audio signal, which is sent from the radio system 865 to the baseband system 870.

If the received signal contains audio information, then baseband system 870 decodes the signal and converts it to an analog signal. Then the signal is amplified and sent to a speaker. The baseband system 870 also receives analog audio signals from a microphone. These analog audio signals are converted to digital signals and encoded by the baseband system 870. The baseband system 870 also codes the digital signals for transmission and generates a baseband transmit audio signal that is routed to the modulator portion of the radio system 865. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 860 where the signal is switched to the antenna port for transmission.

The baseband system 870 is also communicatively coupled with the processor 805. The processor 805 has access to one or more data storage areas including, for example, but not limited to, the main memory 815 and the secondary memory 820. The processor 805 is preferably configured to execute instructions (i.e., computer programs or software) that can be stored in the main memory 815 or in the secondary memory 820. Computer programs can also be received from the baseband processor 870 and stored in the main memory 815 or in the secondary memory 820, or executed upon receipt. Such computer programs, when executed, enable the system 800 to perform the various functions of the present invention as previously described. For example, the main memory 815 may include various software modules (not shown) that are executable by processor 805.

The steps of a method or algorithm or the functions of a module, unit or block described in connection with the embodiments disclosed herein can be embodied directly in hardware, in a software module executed by a processor, or in a combination of the two. Furthermore, those of skill in the art will appreciate that the various illustrative logical blocks, modules, units, and method steps described in connection with the above described figures and the embodiments disclosed herein can often be implemented as electronic hardware, computer software, or combinations of both. To clearly illustrate this interchangeability of hardware and software, various illustrative components, blocks, modules, units, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, unit or step is for ease of description. Specific functions or steps can be moved from one module, block or unit to another without departing from the invention.

The hardware used to implement the various illustrative blocks and modules described in connection with the various embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions preferably configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or implementations of algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; PSTN; or other type of network.

While various embodiments have been described above, it should be understood that they have been presented by way of example only, and not of limitation. The breadth and scope should not be limited by any of the above-described example embodiments. Where this document refers to technologies that would be apparent or known to one of ordinary skill in the art, such technologies encompass those apparent or known to the skilled artisan now or at any time in the future. In addition, the described embodiments are not restricted to the illustrated example architectures or configurations, but the desired features can be implemented using a variety of alternative architectures and configurations. As will become apparent to one of ordinary skill in the art after reading this document, the illustrated embodiments and their various alternatives can be implemented without confinement to the illustrated example. One of ordinary skill in the art would also understand how alternative functional, logical or physical partitioning and configurations could be utilized to implement the desired features of the described embodiments.

Furthermore, although items, elements or components can be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases can be absent.

Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C.

The foregoing method descriptions and the process flow diagrams are provided merely as illustrative examples and are not intended to require or imply that the operations of the various embodiments must be performed in the order presented. As will be appreciated by one of skill in the art the order of operations in the foregoing embodiments may be performed in any order. Words such as "thereafter," "then," "next," etc., are not intended to limit the order of the operations; these words are simply used to guide the reader through the description of the methods. Further, any reference to claim elements in the singular, for example, using the articles "a," "an," or "the" is not to be construed as limiting the element to the singular.

Although particular embodiments have been shown and described, it is to be understood that the above description is not intended to limit the scope of these embodiments. While embodiments and variations of the many aspects of the invention have been disclosed and described herein, such disclosure is provided for purposes of explanation and illustration only. Thus, various changes and modifications may be made without departing from the scope of the claims. For example, not all of the components described in the embodiments are necessary, and the invention may include any suitable combinations of the described components, and the general shapes and relative sizes of the components of the invention may be modified. Accordingly, embodiments are intended to exemplify alternatives, modifications, and equivalents that may fall within the scope of the claims. The invention, therefore, should not be limited, except to the following claims, and their equivalents.

What is claimed is:

1. A system for auto-populating a Disability Benefits Questionnaire (DBQ), the system comprising:
   one or more databases storing disability information related to a plurality of disabilities, a plurality of original DBQs each corresponding to a disability of the plurality of disabilities, a plurality of abbreviated DBQs each corresponding to a disability of the plurality of disabilities, and a plurality of conversion rules each corresponding to an original DBQ of the plurality of original DBQs;
   at least one user interface configured to receive inputs related to a disability; and
   a platform server comprising at least one processor communicatively coupled to the one or more databases and the at least one user interface, the platform server programmed to:
      obtain, via the at least one user interface, data representative of a first disability of the plurality of disabilities,
      retrieve a first abbreviated DBQ of the plurality of abbreviated DBQs and a second abbreviated DBQ of the plurality of abbreviated DBQs based on the first disability represented by the obtained data,
      extract first input data representative of answers input into fields of the first abbreviated DBQ by a first end user and extract second input data representative of answers input into fields of the second abbreviated DBQ by a second end user,
      populate an original DBQ of the plurality of original DBQs based on the first input data and the second input data using conversion rules corresponding to the original DBQ to generate a completed original DBQ, wherein the original DBQ corresponds to the first disability, and wherein the first abbreviated DBQ and the second abbreviated DBQ are truncated versions of the original DBQ, and
      provide the completed original DBQ to the first end user via the at least one user interface.

2. The system of claim 1, wherein the platform server is further configured to derive a potential rating using the first input data and the second input data.

3. The system of claim 2, wherein in order to derive the potential rating, the platform server is further configured to:
   group the plurality of conversion rules into a plurality of symptom groups;
   assign a rating number to each of the plurality of symptom groups; and
   choose the potential rating as the assigned rating of the symptom group with a greatest assigned rating of the plurality of symptom groups with an amount of selected conversion rules above a threshold number of selected conversion rules.

4. The system of claim 1, wherein the platform server is further configured to package the retrieved first abbreviated DBQ into a message and transmit the message to the first end user, wherein the first end user does not have access to the platform server.

5. The system of claim 1, wherein the platform server is further configured to generate a web-based application through which the second end user is authenticated for access to the platform server and submits the second abbreviated DBQ to the platform server, the submitted second abbreviated DBQ comprising inputs into the fields of the second abbreviated DBQ.

6. The system of claim 1, wherein the second end user is a doctor or medical practitioner.

7. The system of claim 6, wherein the second abbreviated DBQ comprises a Patient Evaluation Survey.

8. The system of claim 1, wherein:
   the first abbreviated DBQ and the second abbreviated DBQ are a same abbreviated DBQ, and
   the first abbreviated DBQ and the second abbreviated DBQ include fields for inputs by both the first end user and the second end user.

9. The system of claim 1, wherein the platform server is further configured to send the DBQ to a third end user.

10. The system of claim 9, wherein the third end user is one of an underwriter or an administrator.

11. The system of claim 10, wherein the platform server is further configured to receive a quality control approval from the third end user.

12. The system of claim 9, wherein the platform server is further configured to send the DBQ to a fourth end user.

13. The system of claim 12, wherein the fourth end user is a case manager.

14. The system of claim 1, wherein the plurality of conversion rules map one or more fields of the original DBQ to one or more fields on an abbreviated DBQ.

15. The system of claim 1, wherein the platform server is further configured to determine validity of the first input data and the second input data according to the conversion rules corresponding to the original DBQ.

16. The system of claim 1, wherein:
   the first end user is associated with a user profile comprising information fields, and
   the information fields comprise one or more of: disability information, identifying information, contact information, veteran status information, or authentication information.

17. The system of claim 16, wherein:
   the user profile further comprises an actual rating, and
   the actual rating is representative of all disability claims submitted by the first end user.

18. The system of claim 1, wherein each conversion rule of the plurality of conversion rules corresponds to only one original DBQ of the plurality of original DBQs.

* * * * *